United States Patent
Matilla Dueñas et al.

(10) Patent No.: US 12,371,711 B2
(45) Date of Patent: *Jul. 29, 2025

(54) VECTORS FOR THE TREATMENT OF FRIEDREICH'S ATAXIA

(71) Applicants: FUNDACIÓ INSTITUT D'INVESTIGACIÓ EN CIENCIES DE LA SALUT GERMANS TRIAS I PUJOL, Badalona (ES); GENTEC, S.A., Barcelona (ES)

(72) Inventors: Antoni Matilla Dueñas, Badalona (ES); Ivelisse Sánchez Díaz, Badalona (ES); Eudald Balagué Cabasés, Badalona (ES)

(73) Assignees: FUNDACIÓ INSTITUT D'INVESTIGACIÓ EN CIENCIES DE LA SALUT GERMANS TRIAS I PUJOL, Badalona (ES); GENTEC, S.A., Barcelona (ES)

(*) Notice: Subject to any disclaimer, the term of this patent is extended or adjusted under 35 U.S.C. 154(b) by 482 days.

This patent is subject to a terminal disclaimer.

(21) Appl. No.: 17/741,024

(22) Filed: May 10, 2022

(65) Prior Publication Data

US 2022/0340928 A1    Oct. 27, 2022

Related U.S. Application Data

(63) Continuation of application No. 16/757,263, filed as application No. PCT/EP2018/078384 on Oct. 17, 2018, now Pat. No. 12,084,673.

(30) Foreign Application Priority Data

Oct. 17, 2017    (EP) .................................... 17382691

(51) Int. Cl.
| | |
|---|---|
| *C12N 15/864* | (2006.01) |
| *A61K 48/00* | (2006.01) |
| *A61P 25/00* | (2006.01) |
| *A61P 25/14* | (2006.01) |
| *C12N 15/86* | (2006.01) |

(52) U.S. Cl.
CPC ............ *C12N 15/86* (2013.01); *A61K 48/005* (2013.01); *A61K 48/0058* (2013.01); *A61K 48/0066* (2013.01); *A61P 25/00* (2018.01); *A61P 25/14* (2018.01); *C12N 2750/14143* (2013.01); *C12N 2830/48* (2013.01)

(58) Field of Classification Search
None
See application file for complete search history.

(56) References Cited

U.S. PATENT DOCUMENTS

| | | | |
|---|---|---|---|
| 9,593,312 | B2* | 3/2017 | Björklund .............. A61P 25/36 |
| 2020/0113462 | A1 | 4/2020 | Martínez Piñeiro et al. |
| 2020/0354467 | A1 | 11/2020 | Sarrias Fornés et al. |
| 2021/0189423 | A1 | 6/2021 | Matilla Dueñas et al. |
| 2021/0278405 | A1 | 9/2021 | Izquierdo García et al. |
| 2022/0162699 | A1 | 5/2022 | Beyer et al. |

FOREIGN PATENT DOCUMENTS

| | | |
|---|---|---|
| WO | 2009/034127 A1 | 3/2009 |
| WO | 2016/115503 A1 | 7/2016 |
| WO | 2016/150964 A1 | 9/2016 |

OTHER PUBLICATIONS

Altschul et al., "Basic Local Alignment Search Tool," *J. Mol. Biol.* 215(3):403-410, 1990.
Chapdelaine et al., "Development of an AAV9 coding for a 3XFLAG-TALEfrat#8-VP64 able to increase in vivo the human frataxin in YG8R mice," *Gene Therapy* 23(7):606-614, 2016.
GenBank, "*Homo sapiens* phosphoglycerate kinase 1 (PGK1) gene, partial cds," Accession No. M60581.1, Jul. 26, 2016. (1 page).
Gérard et al., "An AAV9 coding for frataxin clearly improved the symptoms and prolonged the life of Friedreich ataxia mouse models," *Molecular Therapy—Methods & Clinical Development* 1(14044):1-11, 2014.
Mattar et al., "Systemic gene delivery following intravenous administration of AAV9 to fetal and neonatal mice and late-gestation non-human primates," *The FASEB Journal* 29(9):3876-3888, 2015.
Pook et al., "Rescue of the Friedreich's ataxia knockout mouse by human YAC transgenesis," *Neurogenetics* 3(4):185-193, 2001.
Rezaie et al., "Intra-luminal gene therapy in the procine artery using a recombinant adeno-associated virus 9," *Gene* 618:24-27, 2017.
Tremblay et al., "AAV9-Frataxin Reduces the Symptoms and Prolongs the Life of Friedreich Ataxia Mouse Models," *Molecular Therapy* 23 (Supplement 1), 2015 (1 page).
Virmouni et al., "Cellular, Molecular and Functional Characterisation of YAC Transgenic Mouse Models of Friedreich Ataxia," *PLOS ONE* 9(9):e107416, 2014 (13 Pages).

* cited by examiner

*Primary Examiner* — Michael D Burkhart
(74) *Attorney, Agent, or Firm* — Seed IP Law Group LLP

(57) ABSTRACT

The present invention provides gene therapies for the treatment of Friedreich's ataxia. Specifically, the present invention provides a nucleic acid, cloning vector and transfer vector for the production of an adeno-associated virus (AAV) vector. The nucleic acid comprises (i) a nucleic acid sequence encoding frataxin, (ii) a phospho-glycerate-kinase (PGK) promoter, and (iii) a woodchuck hepatitis virus posttranscriptional regulatory element (WPRE). The present invention also provides a pharmaceutical composition which comprises the AAV vector or nucleic acid. Also, the AAV vector, nucleic acid or pharmaceutical composition can be used as a medicament, specifically as a medicament for the treatment of Friedreich's ataxia.

17 Claims, 11 Drawing Sheets
Specification includes a Sequence Listing.

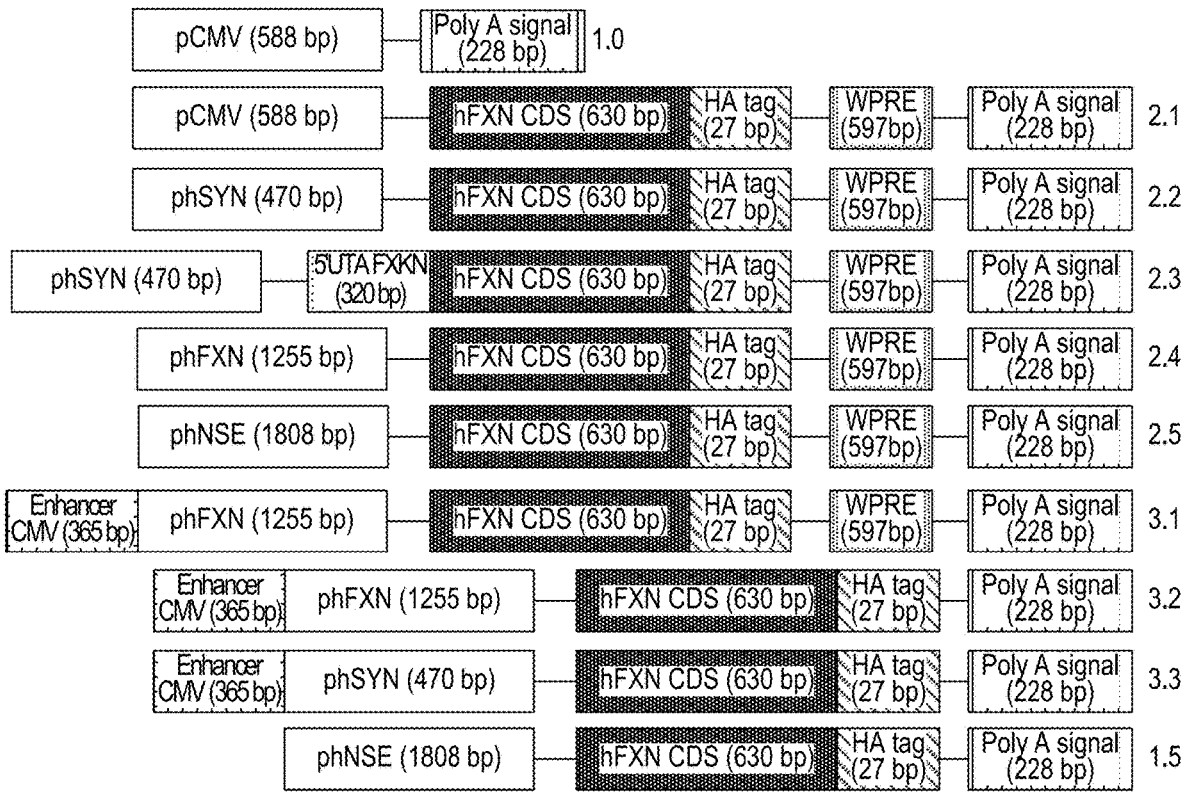

- Cell Type: HEK293
- Quantity of protein loaded: 60 μg
- WB:Anti-HA tag
  1. pcDNA3.1-pCMV-FXN-HA-WPRE (2.1)
  2. pcDNA3.1-phSYN-FXN-HA-WPRE (2.2)
  3. pcDNA3.1-phFXN-FXN-HA-WPRE (2.3)
  4. pcDNA3.1-prNSE-FXN-HA-WPRE (2.4)
  5. pcDNA3.1-E-phFXN-FXN-HA-WPRE (3.1)
  6. pcDNA3.1-E-phFXN-FXN-HA (3.2)
  7. pcDNA3.1-E-phSYN-FXN-HA (3.3)
  8. pcDNA3.1-phNSE-FXN-HA (1.5)
  9. Empty vector (Negative control) 1.0

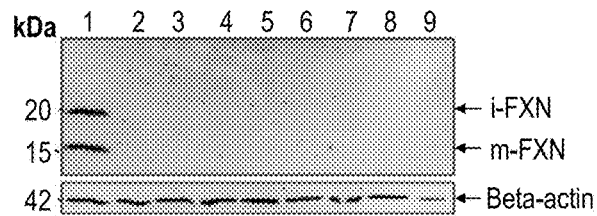

- Cell Type: N2a cells
- Protein quantity: 120 μg
- WB:Anti-HA tag
  1. Empty vector (Negative control) 1.0
  2. pcDNA3.1-pCMV-FXN-HA-WPRE (2.1)
  3. pcDNA3.1-E-phSYN-FXN-HA (3.3)
  4. pcDNA3.1-E-phFXN-FXN-HA (3.2)
  5. pcDNA3.1-phNSE-FXN-HA (1.5)
  6. pcDNA3.1-phNSE-FXN-HA-WPRE (2.4)
  7. pcDNA3.1-phSYN-FXN-HA-WPRE (2.2)
  8. pcDNA3.1-phSYN-5'UTR-FXN-HA-WPRE (2.5)
  9. pcDNA3.1-phFXN-FXN-HA-WPRE (2.3)

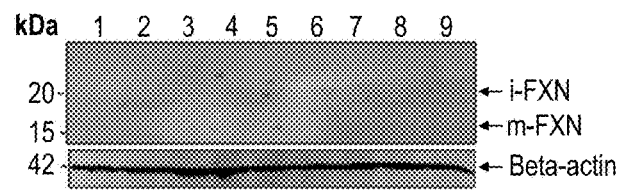

*FIG. 3*

Figure 5:
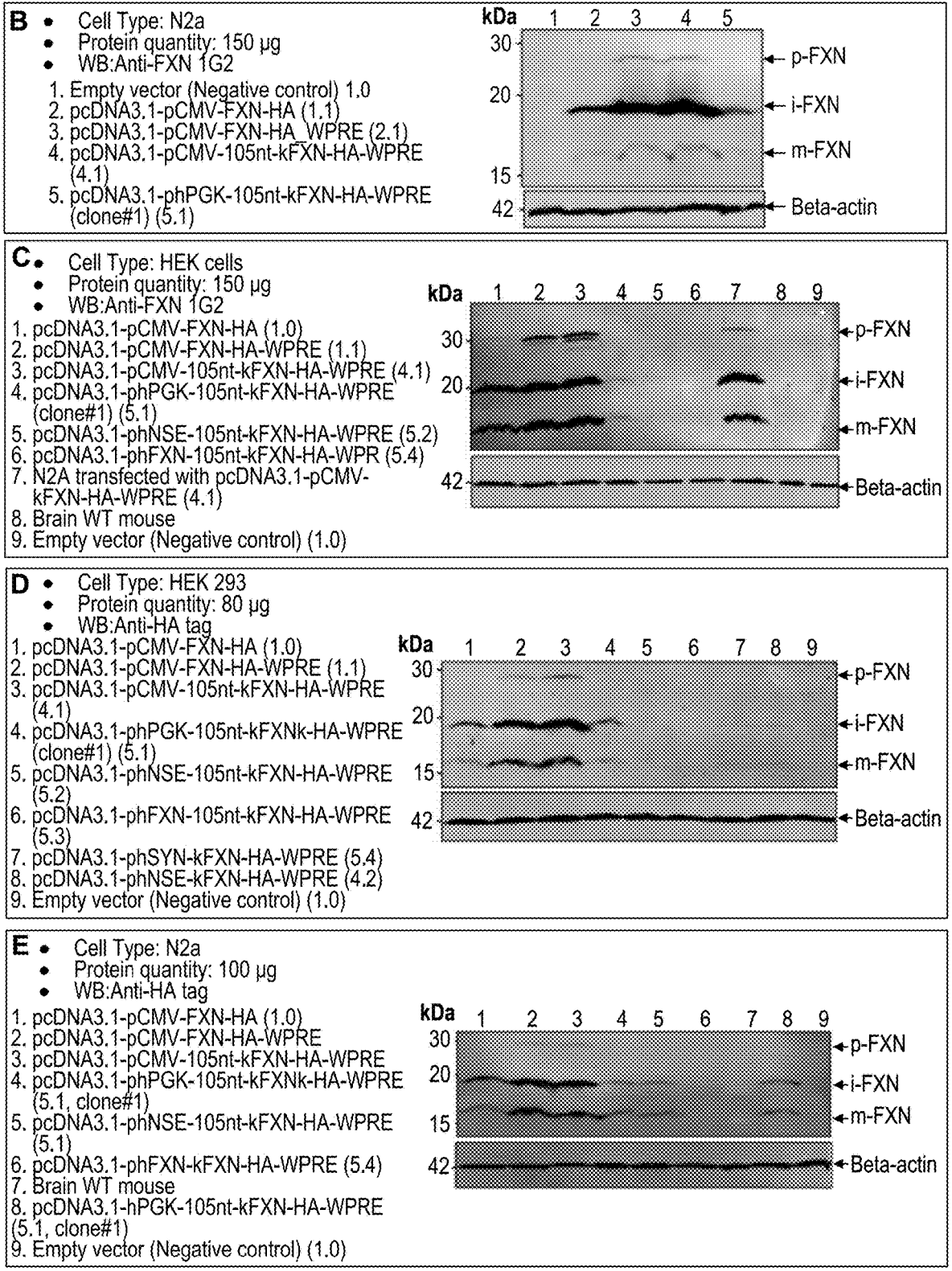

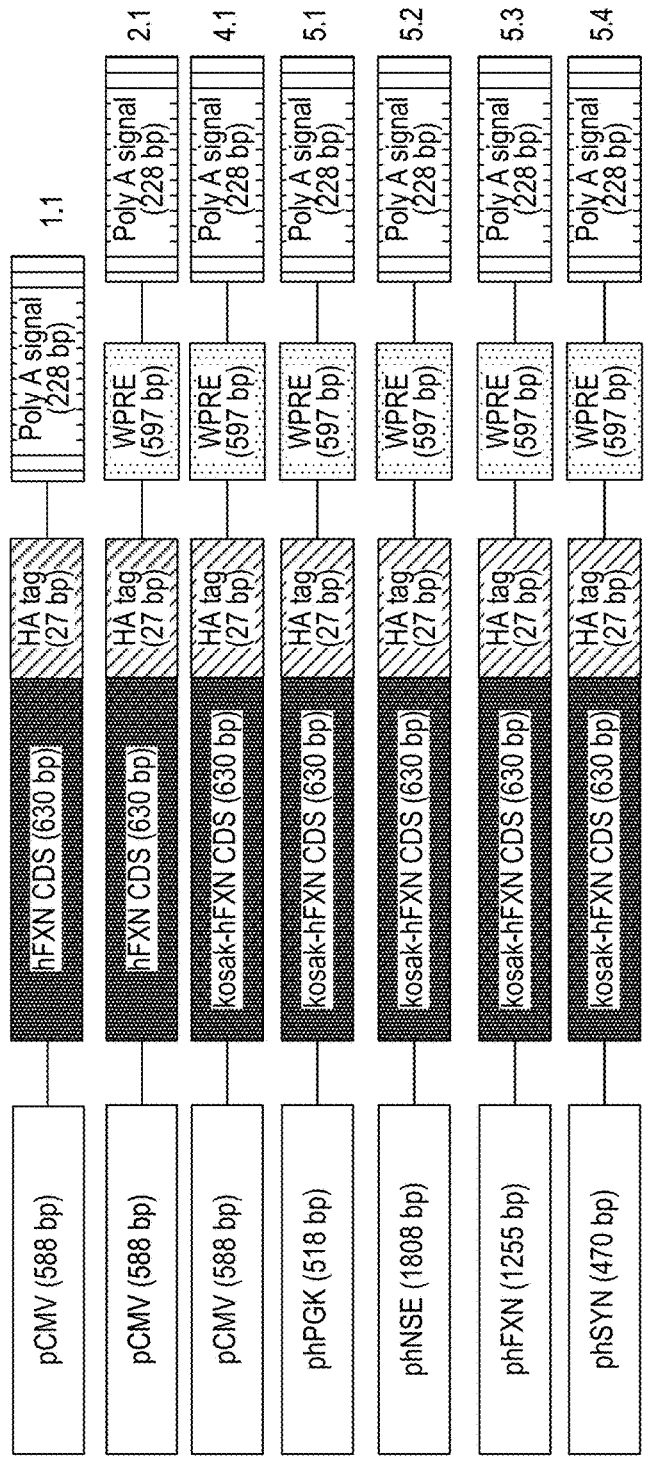
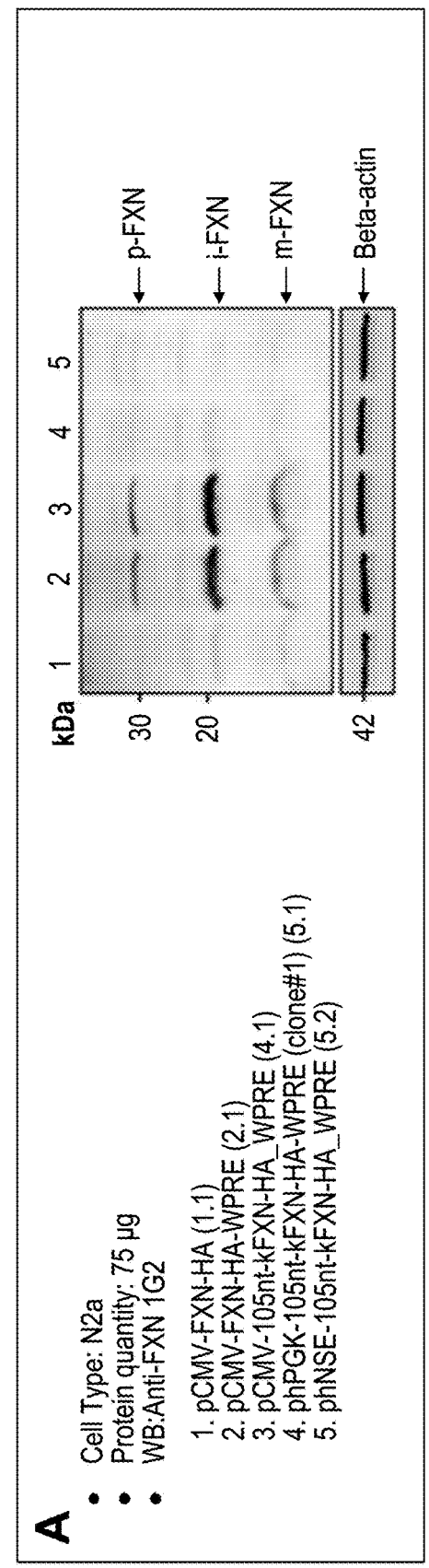
FIG. 5

Figure 6
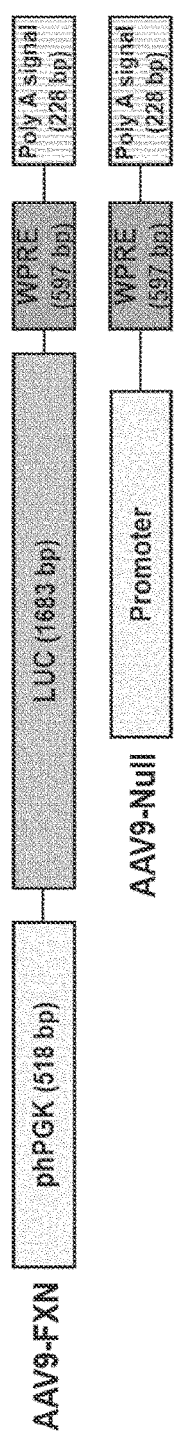
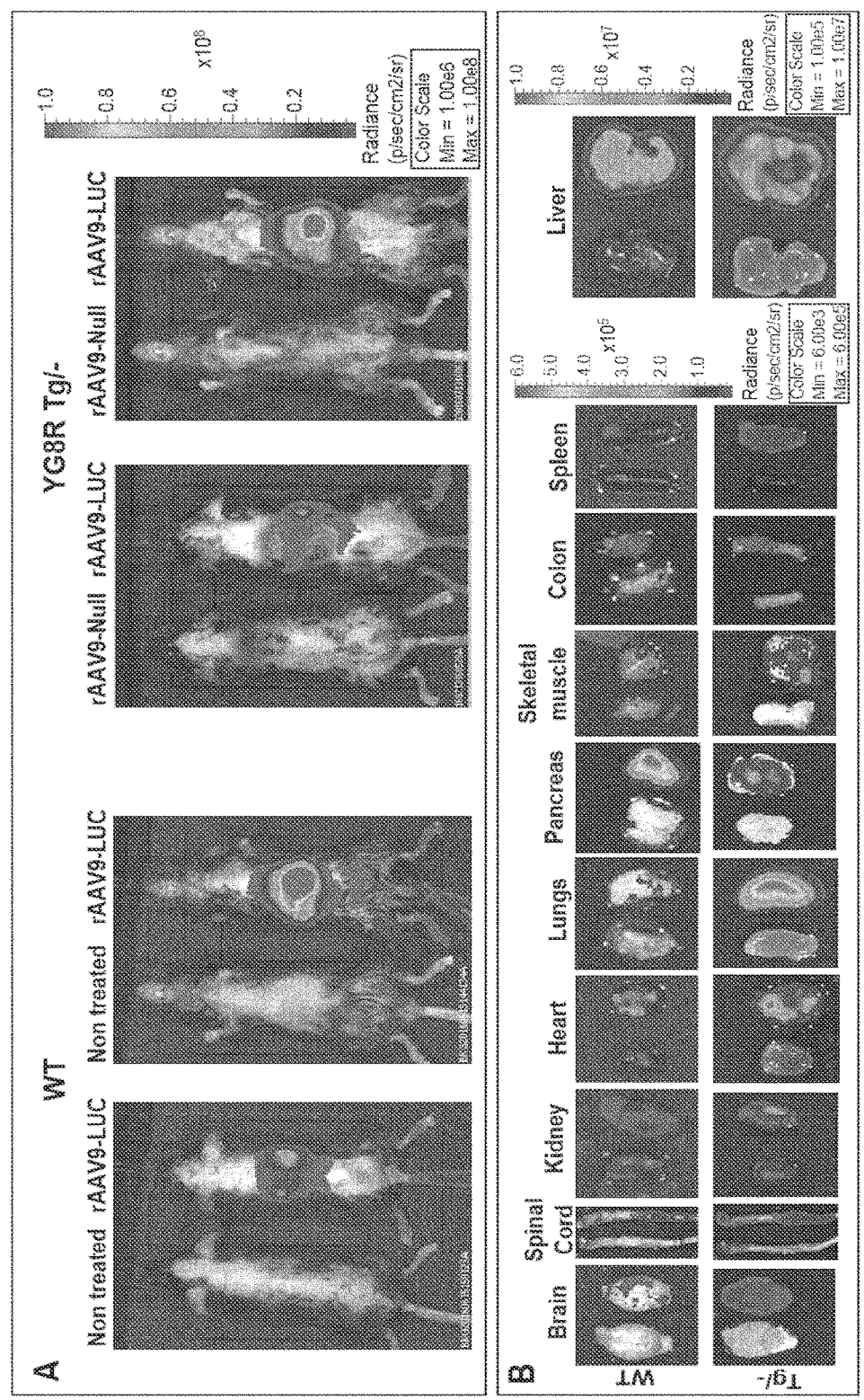

Figure 7

A

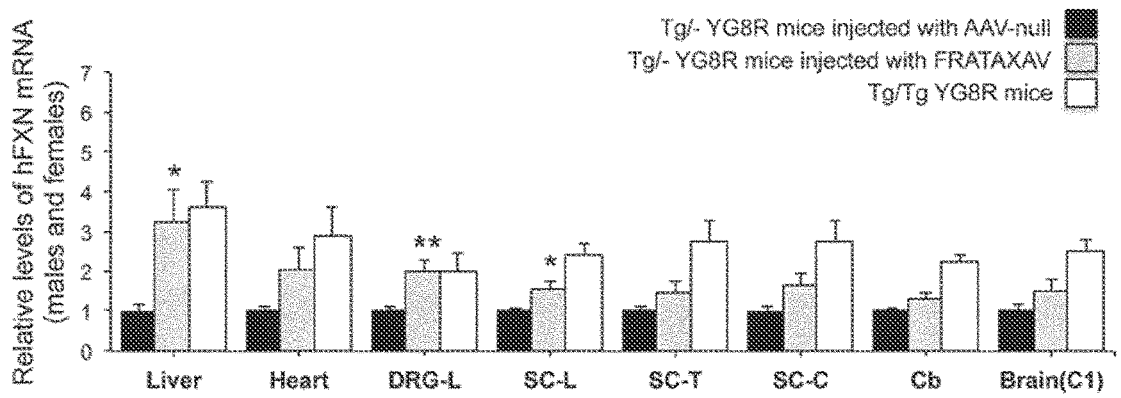

| | Tg/- + AAV-NULL vs Tg/- + AAV-FXN | Tg/- + AAV-FXN vs Tg/Tg |
|---|---|---|
| Liver | 3.23 fold, p=0.019 | 0.349 |
| Heart | 2.02 fold, p= 0.080 | 0.185 |
| DRG (Lumbar) | 2.01 fold, p=0.004 | 0.493 |
| Spinal Cord (Lumbar) | 1.55 fold, p=0.024 | 0.015 |
| Spinal Cord (Thoracic) | 1.46 fold, p=0.104 | 0.027 |
| Spinal Cord (Cervical) | 1.63 fold, p=0.062 | 0.088 |
| Cerebellum | 1.29 fold, p=0.066 | 0.002 |
| Brain C1 | 2.51 fold, p=0.075 | 0.020 |

B

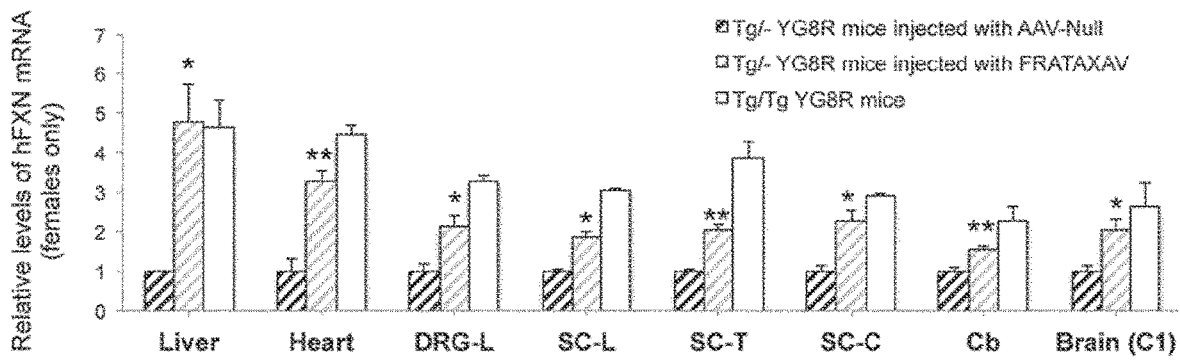

| | Tg/- + AAV-NULL vs Tg/- + AAV-FXN | Tg/- + AAV-FXN vs Tg/Tg |
|---|---|---|
| Liver | 3.23 fold, p=0.027 | 0.454 |
| Heart | 2.02 fold, p=0.007 | 0.018 |
| DRG (Lumbar) | 2.01 fold, p=0.029 | 0.030 |
| Spinal Cord (Lumbar) | 1.55 fold, p=0.010 | 0.001 |
| Spinal Cord (Thoracic) | 1.46 fold, p=0.003 | 0.006 |
| Spinal Cord (Cervical) | 1.63 fold, p=0.012 | 0.026 |
| Cerebellum | 1.29 fold, p=0.008 | 0.077 |
| Brain C1 | 1.63 fold, p=0.029 | 0.207 |

SEQUENCE LISTING

```
<160> NUMBER OF SEQ ID NOS: 12

<210> SEQ ID NO 1
<211> LENGTH: 518
<212> TYPE: DNA
<213> ORGANISM: Artificial Sequence
<220> FEATURE:
<223> OTHER INFORMATION: PGK promoter

<400> SEQUENCE: 1
gaattccggg gttggggttg cgccttttcc aaggcagccc tgggtctgcg cagggacgcg     60
gctgctctgg gcgtggttcc gggaaacgca gcggcgccga ccctgggtct cgcacattct    120
tcacgtccgt tcgcagcgtc acccggatct tcgccgctac ccttgtgggc ccccggcga    180 cgcttcctgc tccgcccta agtcgggaag gttccttgcg gttcgcggcg tgccggacgt    240
gacaaacgga agccgcacgt ctactagta ccctcgcaga cggacagcgc cagggagcaa    300
tggcagcgcg ccgaccgcga tgggctgtgg ccaatagcg ctgctcagca gggcgcgccg    360
agagcagcgg ccgggaaggg gcggtgcggg aggcggggtg tggggcggta gtgtgggccc    420
tgttcctgcc cgcgcggtgt tccgcattct gcaagcctcc ggagcgcacg tcggcagtcg    480
gctccctcgt tgaccgaatc accgacctct ctccccag                            518

<210> SEQ ID NO 2
<211> LENGTH: 597
<212> TYPE: DNA
<213> ORGANISM: Artificial Sequence
<220> FEATURE:
<223> OTHER INFORMATION: WPRE

<400> SEQUENCE: 2
tcgacaatca acctctggat tacaaaattt gtgaaagatt gactggtatt cttaactatg     60
ttgctccttt tacgctatgt ggatacgctg ctttaatgcc tttgtatcat gctattgctt    120
cccgtatggc tttcattttc tcctccttgt ataaatcctg gttgctgtct ctttatgagg    180
agttgtggcc cgttgtcagg caacgtggcg tggtgtgcac tgtgtttgct gacgcaaccc    240
ccactggttg gggcattgcc accacctgtc agctcctttc cgggactttc gctttccccc    300
tccctattgc cacggcggaa ctcatcgccg cctgccttgc ccgctgctgg acagggctc    360 ggctgttggg cactgacaat tccgtggtgt tgtcggggaa gctgacgtcc tttccatggc    420
tgctcgcctg tgttgccacc tggattctgc gcgggacgtc cttctgctac gtcccttcgg    480
```

```
cectcaatcc agcggacctt ccttcccgcg gcctgctgcc ggctctgcgg cctcttccgc    540
gtcttcgcct tcgccctcag acgagtcgga tctccctttg gccgcctcc ccgcctg       597
```

<210> SEQ ID NO 3
<211> LENGTH: 631
<212> TYPE: DNA
<213> ORGANISM: Artificial Sequence
<220> FEATURE:
<223> OTHER INFORMATION: frataxin

<400> SEQUENCE: 3

```
atgtggactc tcgggcgccg cgcagtagcc ggcctcctgg cgtcacccag cccggcccag     60
gcccagaccc tcacccgggt cccgcggccg gcagagttgg ccccactctg cggccgccgt    120
ggcctgcgca ccgacatcga tgcgacctgc acgccccgcc gcgcaagttc gaaccagaga    180
ggtctcaacc agatttggaa tgtcaaaaag cagagtgtct atttgatgaa tttgaggaaa    240
tctggaactt gggccaccc aggctctcta gatgagacca cctatgaaag actagcagag    300
gaaacgctgg actctttagc agagttttttt gaagaccttg cagacaagcc atacacgttt    360
gaggactatg atgtctcctt tgggagtggt gtcttaactg tcaaactggg tggagatcta    420
ggaacctatg tgatcaacaa gcagacgcca acaagcaaa tctggctatc ttctccatcc     480
agtggaccta gcgttatga ctggactggg aaaaactggg tgtactccca cgacggcgtg    540
tccctccatg agctgctggc cgcagagctc actaaagcct taaaaaccaa actggacttg    600
tcttccttgg cctattccgg aaaagatgct t                                    631
```

<210> SEQ ID NO 4
<211> LENGTH: 1934
<212> TYPE: DNA
<213> ORGANISM: Artificial Sequence
<220> FEATURE:
<223> OTHER INFORMATION: PGK frataxin and WPRE cassette

<400> SEQUENCE: 4

```
gaattccggg gttggggttg cgccttttcc aaggcagccc tgggtctgcg cagggacgcg     60
gctgctctgg gcgtggttcc gggaaacgca gcggcgccga ccctgggtct cgcacattct    120
tcacgtccgt tcgcagcgtc acccggatct tcgccgctac ccttgtgggc ccccggcga    180 cgcttcctgc tccgcccta agtcgggaag gttccttgcg gttcgcggcg tgccggacgt    240
gacaaacgga agccgcacgt ctcactagta ccctcgcaga cggacagcgc cagggagcaa    300
tggcagcgcg ccgaccgcga tgggctgtgg ccaatagcgg ctgctcagca gggcgcgccg    360
agagcagcgg ccgggaaggg gcggtgcggg aggcggggtg tggggcggta gtgtgggccc    420
tgttcctgcc cgcgcggtgt tccgcattct gcaagcctcc ggagcgcacg tcggcagtcg    480
gctccctcgt tgaccgaatc accgacctct ctccccagtg gctaactaga aacccactg    540 cttactggct tatcgaaatt aatacgactc actataggga gacccaagct ggctagcgtt    600
taaacttaag cttggccgcc accatgtgga ctctcgggcg ccgcgcagta gccggcctcc    660
tggcgtcacc cagcccggcc caggcccaga ccctcacccg gtccgcgg ccggcagagt    720 tggccccact ctgcggccgc cgtggcctgc gcaccgacat cgatgcgacc tgcacgcccc    780
gccgcgcaag ttcgaaccag agaggtctca accagatttg gaatgtcaaa aagcagagtg    840
tctatttgat gaatttgagg aaatctggaa ctttgggcca cccaggctct ctagatgaga    900
ccacctatga aagactagca gaggaaacgc tggactcttt agcagagtt tttgaagacc    960
```

| | |
|---|---|
| ttgcagacaa gccatacacg tttgaggact atgatgtctc ctttgggagt ggtgtcttaa | 1020 |
| ctgtcaaact gggtggagat ctaggaacct atgtgatcaa caagcagacg ccaaacaagc | 1080 |
| aaatctggct atcttctcca tccagtggac ctaagcgtta tgactggact gggaaaaact | 1140 |
| gggtgtactc ccacgacggc gtgtccctcc atgagctgct ggccgcagag ctcactaaag | 1200 |
| ccttaaaaac caaactggac ttgtcttcct tggcctattc cggaaaagat gctttgccca | 1260 |
| cctagggatc ggatcccgg gtaccgagct cgaattctgc agatatccag cacactttgc | 1320 |
| ctttctctcc acaggtgtcg acaatcaacc tctggattac aaaatttgtg aaagattgac | 1380 |
| tggtattctt aactatgttg ctccttttac gctatgtgga tacgctgctt taatgccttt | 1440 |
| gtatcatgct attgcttccc gtatggcttt cattttctcc tccttgtata atcctggtt | 1500 |
| gctgtctctt tatgaggagt tgtggcccgt tgtcaggcaa cgtggcgtgg tgtgcactgt | 1560 |
| gtttgctgac gcaaccccca ctggttgggg cattgccacc acctgtcagc tcctttccgg | 1620 |
| gactttcgct ttccccctcc ctattgccac ggcggaactc atcgccgcct gccttgcccg | 1680 |
| ctgctggaca ggggctcggc tgttgggcac tgacaattcc gtggtgttgt cggggaagct | 1740 |
| gacgtccttt ccatggctgc tcgcctgtgt tgccacctgg attctgcgcg gacgtccttt | 1800 |
| ctgctacgtc ccttcggccc tcaatccagc ggaccttcct tcccgcggcc tgctgccggc | 1860 |
| tctgcggcct cttccgcgtc ttcgccttcg ccctcagacg agtcggatct ccctttgggc | 1920 |
| cgcctccccg cctg | 1934 |

<210> SEQ ID NO 5
<211> LENGTH: 2458
<212> TYPE: DNA
<213> ORGANISM: Artificial Sequence
<220> FEATURE:
<223> OTHER INFORMATION: ITR PGK frataxin WPRE PolyA ITR

<400> SEQUENCE: 5

| | |
|---|---|
| ctggcgcgct cgctcgctca ctgaggccgc ccgggcaaag cccggcgtc gggcgacctt | 60 |
| tggtcgcccg gcctcagtga gcgagcgagc gcgcagagag ggagtggcca actccatcac | 120 |
| taggggttcc tgaattccgg ggttgggtt gcgccttttc caaggcagcc ctgggtctgc | 180 |
| gcagggacgc ggctgctctg ggcgtggttc cgggaaacgc agcggcgccg accctgggtc | 240 |
| tcgcacattc ttcacgtccg ttcgcagcgt caccccggatc ttcgccgcta cccttgtggg | 300 |
| cccccggcg acgcttcctg ctccgcccct aagtcgggaa ggttccttgc ggttcgcggc | 360 |
| gtgccggacg tgacaaacgg aagccgcacg tctcactagt accctcgcag acggacagcg | 420 |
| ccagggagca atggcagcgc gccgaccgcg atgggctgtg gccaatagcg gctgctcagc | 480 |
| agggcgcgcc gagagcagcg gccgggaagg ggcggtgcgg gaggcggggt gtggggcggt | 540 |
| agtgtgggcc ctgttcctgc ccgcgcggtg ttccgcattc tgcaagcctc cggagcgcac | 600 |
| gtcggcagtc ggctccctcg ttgaccgaat caccgacctc tctccccagt ggctaactag | 660 |
| agaacccact gcttactggc ttatcgaaat taatacgact cactataggg agacccaagc | 720 |
| tggctagcgt ttaaacttaa gcttggccgc caccatgtgg actctcgggc gccgcgcagt | 780 |
| agccggcctc ctggcgtcac ccagcccggc ccagcccag accctcaccc gggtcccgcg | 840 |
| gccggcagag ttggccccac tctgcggccg ccgtggcctg cgcaccgaca tcgatgcgac | 900 |
| ctgcacgccc gccgcgcaa gttcgaacca gagaggtctc aaccagattt ggaatgtcaa | 960 |
| aaagcagagt gtctatttga tgaatttgag gaaatctgga actttgggcc acccaggctc | 1020 |
| tctagatgag accacctatg aaagactagc agaggaaacg ctggactctt tagcagagtt | 1080 |

| | |
|---|---|
| ttttgaagac cttgcagaca agccatacac gtttgaggac tatgatgtct cctttgggag | 1140 |
| tggtgtctta actgtcaaac tgggtggaga tctaggaacc tatgtgatca acaagcagag | 1200 |
| gccaaacaag caaatctggc tatcttctcc atccagtgga cctaagcgtt atgactggac | 1260 |
| tgggaaaaac tgggtgtact cccacgacgg cgtgtccctc catgagctgc tggccgcaga | 1320 |
| gctcactaaa gccttaaaaa ccaaactgga cttgtcttcc ttggcctatt ccggaaaaga | 1380 |
| tgctttgccc acctagggat cggatccccg ggtaccgagc tcgaattctg cagatatcca | 1440 |
| gcacactttg cctttctctc cacaggtgtc gacaatcaac ctctggatta caaaatttgt | 1500 |
| gaaagattga ctggtattct taactatgtt gctccttta cgctatgtgg atacgctgct | 1560 |
| ttaatgcctt tgtatcatgc tattgcttcc cgtatggctt tcattttctc ctccttgtat | 1620 |
| aaatcctggt tgctgtctct ttatgaggag ttgtggcccg ttgtcaggca acgtggcgtg | 1680 |
| gtgtgcactg tgtttgctga cgcaaccccc actggttggg gcattgccac cacctgtcag | 1740 |
| ctccttccg ggactttcgc tttccccctc cctattgcca cggcggaact catcgccgcc | 1800 |
| tgccttgccc gctgctggac aggggctcgg ctgttgggca ctgacaattc cgtggtgttg | 1860 |
| tcggggaagc tgacgtcctt tccatggctg ctcgcctgtg ttgccacctg gattctgcgc | 1920 |
| gggacgtcct tctgctacgt cccttcggcc ctcaatccag cggaccttcc ttcccgcggc | 1980 |
| ctgctgccgg ctctgcggcc tcttccgcgt cttcgccttc gccctcagac gagtcggatc | 2040 |
| tccctttggg ccgcctcccc gcctggaatt cgagctcggt acgatcagct gatcagcctc | 2100 |
| gactgtgcct tctagttgcc agccatctgt tgtttgcccc tcccccgtgc cttccttgac | 2160 |
| cctggaaggt gccactccca ctgtcctttc ctaataaaat gaggaaattg catcgcattg | 2220 |
| tctgagtagg tgtcattcta ttctgggggg tggggtgggg caggacagca aggggaggga | 2280 |
| ttgggaagac aatagcaggc atgctgggga tgcggtgggc tctatggctg cgcgctcgc | 2340 |
| tcgctcactg aggccgcccg ggcaaagccc gggcgtcggg cgacctttgg tcgcccggcc | 2400 |
| tcagtgagcg agcgagcgcg cagagaggga gtggccaact ccatcactag gggttcct | 2458 |

```
<210> SEQ ID NO 6
<211> LENGTH: 105
<212> TYPE: DNA
<213> ORGANISM: Artificial Sequence
<220> FEATURE:
<223> OTHER INFORMATION: Linker

<400> SEQUENCE: 6
```

| | |
|---|---|
| tggctaacta gagaacccac tgcttactgg cttatcgaaa ttaatacgac tcactatagg | 60 |
| gagacccaag ctggctagcg tttaaactta agcttggccg ccacc | 105 |

```
<210> SEQ ID NO 7
<211> LENGTH: 27
<212> TYPE: DNA
<213> ORGANISM: Artificial Sequence
<220> FEATURE:
<223> OTHER INFORMATION: hFXN_Tg_FW

<400> SEQUENCE: 7
```

| | |
|---|---|
| gaacttcaaa ttagttcccc tttcttc | 27 |

```
<210> SEQ ID NO 8
<211> LENGTH: 21
<212> TYPE: DNA
<213> ORGANISM: Artificial Sequence
<220> FEATURE:
```

```
<223> OTHER INFORMATION: hFXN_Tg_RV

<400> SEQUENCE: 8
cacagccatt ctttgggttt c                                              21

<210> SEQ ID NO 9
<211> LENGTH: 18
<212> TYPE: DNA
<213> ORGANISM: Artificial Sequence
<220> FEATURE:
<223> OTHER INFORMATION: IC_FW

<400> SEQUENCE: 9
cacgtgggct ccagcatt                                                  18

<210> SEQ ID NO 10
<211> LENGTH: 22
<212> TYPE: DNA
<213> ORGANISM: Artificial Sequence
<220> FEATURE:
<223> OTHER INFORMATION: IC_RV

<400> SEQUENCE: 10
tcaccagtca tttctgcctt tg                                             22

<210> SEQ ID NO 11
<211> LENGTH: 29
<212> TYPE: DNA
<213> ORGANISM: Artificial Sequence
<220> FEATURE:
<223> OTHER INFORMATION: GAA-F

<400> SEQUENCE: 11
gggattggtt gccagtgctt aaaagttag                                      29

<210> SEQ ID NO 12
<211> LENGTH: 30
<212> TYPE: DNA
<213> ORGANISM: Artificial Sequence
<220> FEATURE:
<223> OTHER INFORMATION: GAA-R

<400> SEQUENCE: 12
gatctaagga ccatcatggc cacacttgcc                                     30
```

VECTORS FOR THE TREATMENT OF FRIEDREICH'S ATAXIA

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 370091_401C1_SEQUENCE_LISTING.txt. The text file is 10 KB, was created on May 10, 2022, and is being submitted electronically via EFS-Web.

TECHNICAL FIELD

The present invention can be included in the field of new therapeutics for the treatment of Freidreich's ataxia. Specifically the present application relates to new products for gene therapy. The products are capable of treating Friedreich's ataxia.

BACKGROUND ART

Friedreich's ataxia (FRDA; OMIM #229300) is a rare inherited neurodegenerative disease that causes progressive damage to the nervous system resulting in symptoms ranging from gait disturbances and language problems to heart disease or cardiomyopathy. The disease was named after the physician Nikolaus Friedreich, who was the first to describe it in the 1860s. Ataxia, referred to problems of motor coordination such as awkward movements and instability, occurs in Friedreich's ataxia by degeneration of nervous tissue in the spinal cord and nerves that control the muscular movement of the arms and legs. The spinal cord shrinks with nerve cells losing part of their myelin sheath. Friedreich's ataxia, although uncommon, is the most common hereditary ataxia, ranging from 1 in 30,000-50,000 live births, with a prevalence of 2-4 per 100,000. Both sexes are affected equally. Symptoms usually begin between 5 and 15 years of age but may, on rare occasions, appear as early as 18 months or as late as 50 years of age. The first symptom that appears is usually difficulty walking, or gait ataxia. Ataxia gradually worsens and spreads slowly to the arms and then to the trunk. Foot deformities such as pes cavus, involuntary folding of the toes, or hammer toes may appear as early signs. Over time, the muscles begin to weaken and to be consumed, especially in the feet, legs and hands, and the deformities develop. Other symptoms include loss of tendon reflexes, especially in the knees and ankles. There is often a gradual loss of sensation in the extremities, which can spread to other parts of the body. Dysarthria develops, and the patient gets tired easily. The rapid, rhythmic and involuntary movements of the eyes called nystagmus are common. Most people with Friedreich's ataxia develop scoliosis, which if severe, can affect breathing.

Other symptoms that can occur are chest pain, shortness of breath and palpitations. These symptoms are the result of various forms of heart disease that often accompany Friedreich's ataxia, such as hypertrophic cardiomyopathy, myocardial fibrosis, or heart failure. Heart rate abnormalities such as tachycardia and heart block are also common. About 20% of people with Friedreich's ataxia develop carbohydrate intolerance and 30% show diabetes mellitus. Some affected people lose hearing or sight. The speed of disease progression varies from person to person. Generally between 10 and 20 years after the onset of the first symptoms, the person is confined to a wheelchair, and in later stages of the disease individuals become totally disabled. Life expectancy may be affected. Many people with Friedreich's ataxia die in adulthood due to associated heart disease, the most common cause of death. However, some people with less severe symptoms of Friedreich's ataxia sometimes live to 60 or 70 years.

Neuroimaging such as MRI shows normal appearance in the early stages of the disease, although progressively reveals variable atrophy of the cervical spinal cord and cerebellum. This often shows atrophy of the superior peduncle. Electrophysiological studies show conduction velocities greater than 40 m/s with absence or reduction of sensory action potentials, and absence of reflex H. At the neuropathological level, marked atrophy of the spinal cord, posterior roots, occasionally of the cerebellum, and cardiac hypertrophy are observed. Neurodegeneration is identified in peripheral sensory nerves with progressive loss of large dorsal root ganglion sensory neurons, dorsal column degeneration, transynaptic degeneration of neurons in Clarke's spine and spinocerebellar fibers, pyramidal tracts, and atrophy of the gracile and cuneiform nuclei. Secondary lesions may include atrophy of the dentate nucleus in the cerebellum affecting large glutamatergic neurons, and atrophy of Betz cells and corticospinal tracts.

In 1996, the cause of Friedreich's ataxia was identified as a molecular defect in the FXN gene located on chromosome 9 (9q21 band). The mutation consists of an abnormal homozygous expansion of the GAA triplet located inside an ALU sequence in the first intron of the FXN gene. About 98% of patients with FRDA have 2 chromosomes with a number between 201 and 1,700 GAA repeats (more frequently between 600 and 900) in each of them. However, 2-5% of patients with FRDA present a GAA expansion and a point mutation in the FXN gene in composite heterozygosis (Table 1). To date, more than 17 different mutations in the FXN gene have been described capable of triggering FRDA. The GAA expansion in FRDA is very unstable during meiosis and interferes with FXN gene transcription causing abnormally low levels of frataxin mRNA. GAA expansion would silence transcription of the FXN gene and thus abolish frataxin expression by forming triple DNA structures or DNA-RNA hybrids, or both. More recently, it has been proposed that the GAA expansion would block the transition from initiation to elongation of transcription due to the formation of heterochromatin-like structures in the vicinity of GAA hyperexpansion. It has also been proposed that GAA expansion would lead to epigenetic methylation of the CpG sites located in the 5' upstream region of the FXN gene causing their silencing. Thus, as a consequence of the GAA mutation in the FXN gene, a deficiency of the frataxin protein occurs in FRDA.

TABLE 1

Most prevalent allelic variants identified
in the FXN gene causing Friedreich's ataxia.

| OMIM | DISEASE ALLELIC VARIANT |
|---|---|
| 606829.0001 | GAA expansion within intron 1 |
| 606829.0002 | Transversion within exon 3: LEU106X |
| 606829.0003 | Transition c.385-2A > G affecting splicing |
| 606829.0004 | Missense variant: Ile154Phe in exon 4 |
| 606829.0005 | Missense mutation: Gly130Val |
| 606829.0006 | Missense mutation affecting start codon: Met1Ile |
| 606829.0007 | Missense mutation: Trp173Gly |
| 606829.0008 | Deletion of 1 nt in codon 75 provoking protein truncation |
| 606829.0009 | Deletion of 6 nt and insertion of 15 nt (c.371_376del6ins15) in exon 3 |

The FXN gene encodes a small conserved mitochondrial protein that contains 210 amino acids (aa) in its precursor form, with a molecular weight of 23,135 Da named frataxin (Q16595). This precursor protein form contains an N-terminal sequence of transit that directs it to the mitochondrial matrix where the mitochondrial peptidase converts it into different smaller isoforms (FXN42-210, FXN56-210, FXN81-210, FXN78-210) of the mature protein frataxin being the FXN81-210 of 130 aa and 14.2 kDa the most abundant. In humans, frataxin is detected in the mitochondrial matrix in association with its inner membrane in a large variety of tissues, and the most abundant levels are identified in cardiac tissue, spinal cord and dividing lymphoblasts, and remarkably the lowest levels in the cerebellum. Frataxin has not been detected in the cerebral cortex to date. Since the gene responsible for the disease was identified and with the generation of several animal models, different functions have been postulated for frataxin such as mitochondrial iron homeostasis, iron storage, response to oxidative stress, biogenesis of Fe—S clusters, modulation of mitochondrial aconitase activity and regulation of oxidative phosphorylation. In FRDA, frataxin deficiency produced by homozygosis expansion of the GAA expansion in the FXN gene leads to insufficient biosynthesis of the iron-sulphur clusters necessary for electron transport in the mitochondria and aconitase assembly leading to dysregulation of mitochondrial function and mitochondrial iron accumulation by alterations of its homeostasis. Frataxin also modulates the DNA binding capacity of the protein aconitase 1 (ACO1), which in addition to participating in the cycle of citric acid in the mitochondrial matrix, regulates the uptake and utilization of cellular iron.

Several animal and cellular models for Friedreich's ataxia have been generated by genetic manipulation. Generating an AF model in the mouse mimicking as close as possible the human disease has been an arduous task, and currently there are 8 distinct murine models of FRDA. Unfortunately none of them present with the combination of all the phenotypic symptoms of FA in the same animal such as lesions in the dorsal root ganglia (DRG) and cerebellar dentate nuclei, although they are useful for the study of isolated aspects of the molecular neurodegenerative process in FRDA and for the evaluation of different treatments in specific symptoms. The most used in pre-clinical treatments are the Prp-CreERT and YG8R mice. The Prp-CreERT mice specifically develop cerebellar and progressive sensory ataxia, the most prominent neurological functions of Friedreich's Ataxia. Histological studies in these animals show abnormalities of the spinal cord and dorsal root ganglia with absence of motor neuropathy, a hallmark of human disease, as well as arborisation defects in Purkinje cells of the cerebellum. In contrast, YG8R transgenic mice in the absence of the endogenous murine frataxin protein exhibit slowly progressive FRDA pathology. In contrast to humans, these mice do not show cardiac deficits.

Among viral and non-viral vectors used in gene therapy for human pathologies, vectors derived from adeno-associated virus (AAV) have shown important clinical benefits and prolonged expressions in animal models of Gaucher disease, Fabry disease, Pompe disease, Metachromatic leukodystrophy, Niemann-Pick A disease and mucopolysaccharidosis I, II, III A, III B, IV and VII among others. Intravenous administration of AAV vectors in animal models of lysosomal storage diseases has led to increases in enzyme activity of up to 16 times normal values in blood, liver, spleen, kidney and muscle, making them very useful for treating this type of pathologies. Over the past 10 years, AAVs have been the vectors of choice in most clinical trials conducted to treat central and peripheral nervous system pathologies (http://www.abedia.com/wiley/index.html). Importantly, no adverse effects have been observed with these vectors to date and the results are very promising. Thus, several factors have made AAVs become the ideal gene delivery vehicle for the central nervous system (CNS). Adeno-associated virus vectors comprising a frataxin sequence have been used to treat FRDA in mice (Gérard et al., 2014. Mol Ther Methods Clin Dev. 1: 14044; Chapdelaine et al., 2016. Gene Ther. 23(7): 606-614; Tremblay et al., 2015. Mol Ther. 23(Suppl. 1): pS153; WO 2016/150964). But, the AAV vectors disclosed in the prior art either over- or under-express frataxin and do not reach all target cells and neurons affected in FRDA, which make them unsuitable for the efficient treatment of FRDA and in particular its neurological signs. Thus, an AAV vector expressing the frataxin protein at a therapeutically effective amount is needed.

At present there is no effective therapy for the treatment of FRDA and therefore there is a need for new therapeutics for the treatment of FRDA. It is an objective of the present invention to provide a suitable therapy for treating FRDA.

FIGURES

Figure 1:
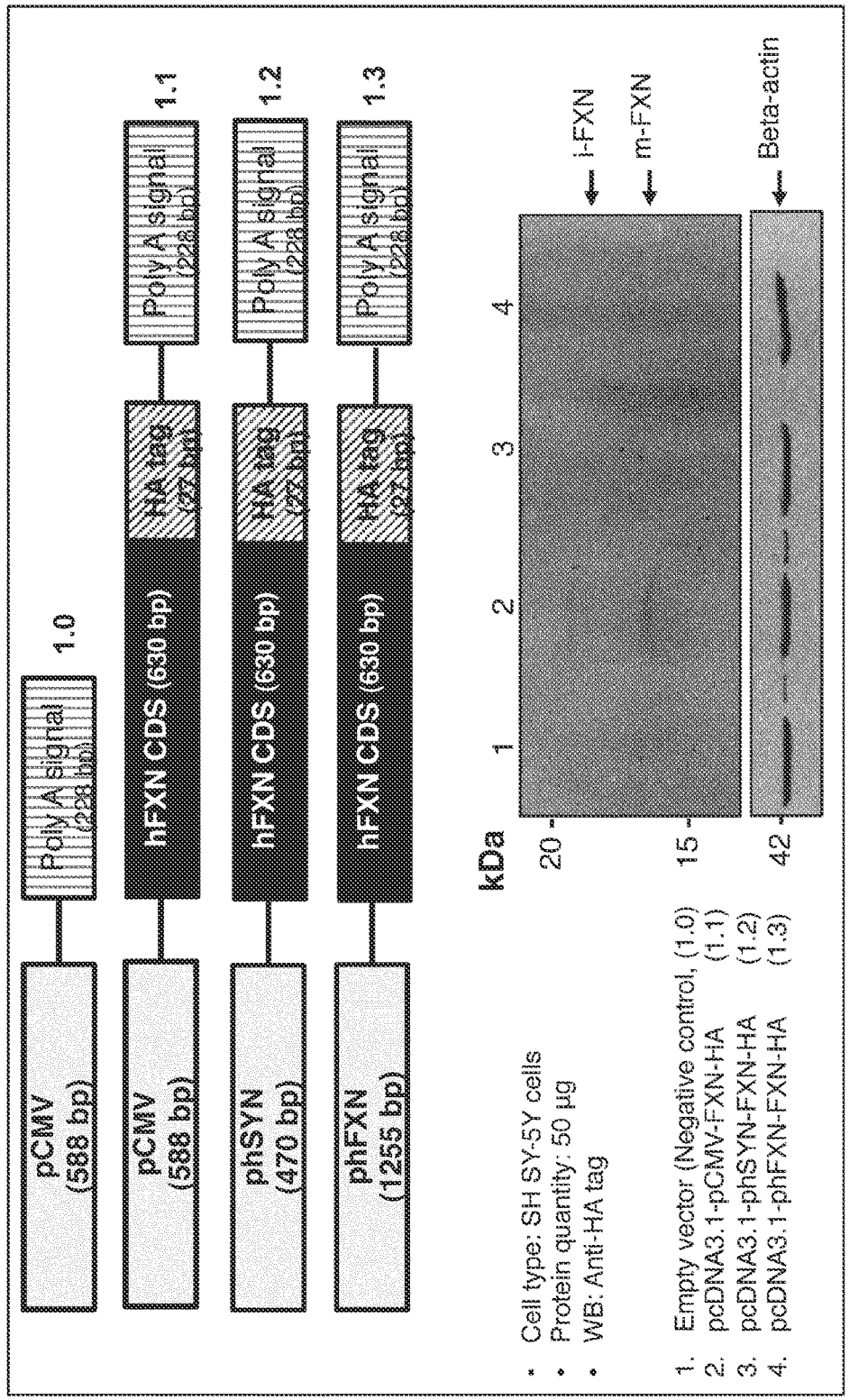

FIG. 1. Evaluation of the SYN (synapsin) and FXN (frataxin; 1,255 bp) human promoters on frataxin (FXN) protein expression. To test the levels of human frataxin (FXN) protein expression under the regulation of a fragment of the endogenous promoter (phFXN), and the synapsin neuronal promoter (phSYN), in comparison to the expression under the high-expressing constitutive promoter CMV, Human Neuroblastoma SH-SY5Y cells were transfected with empty vector (lane 1), or constructs encoding the human synapsin (phSYN) (lane 3), or a 1,255 bp fragment of the frataxin (phFXN) promoters (lane 4). Constructs 1.2 and 1.3 using the phSYN or the phFXN (1,255 bp) to express the human FXN coding sequence (hFXN CDS) did not result in expression of the recombinant frataxin protein (rFXN). HA, hemagglutinin tag.

Figure 2:
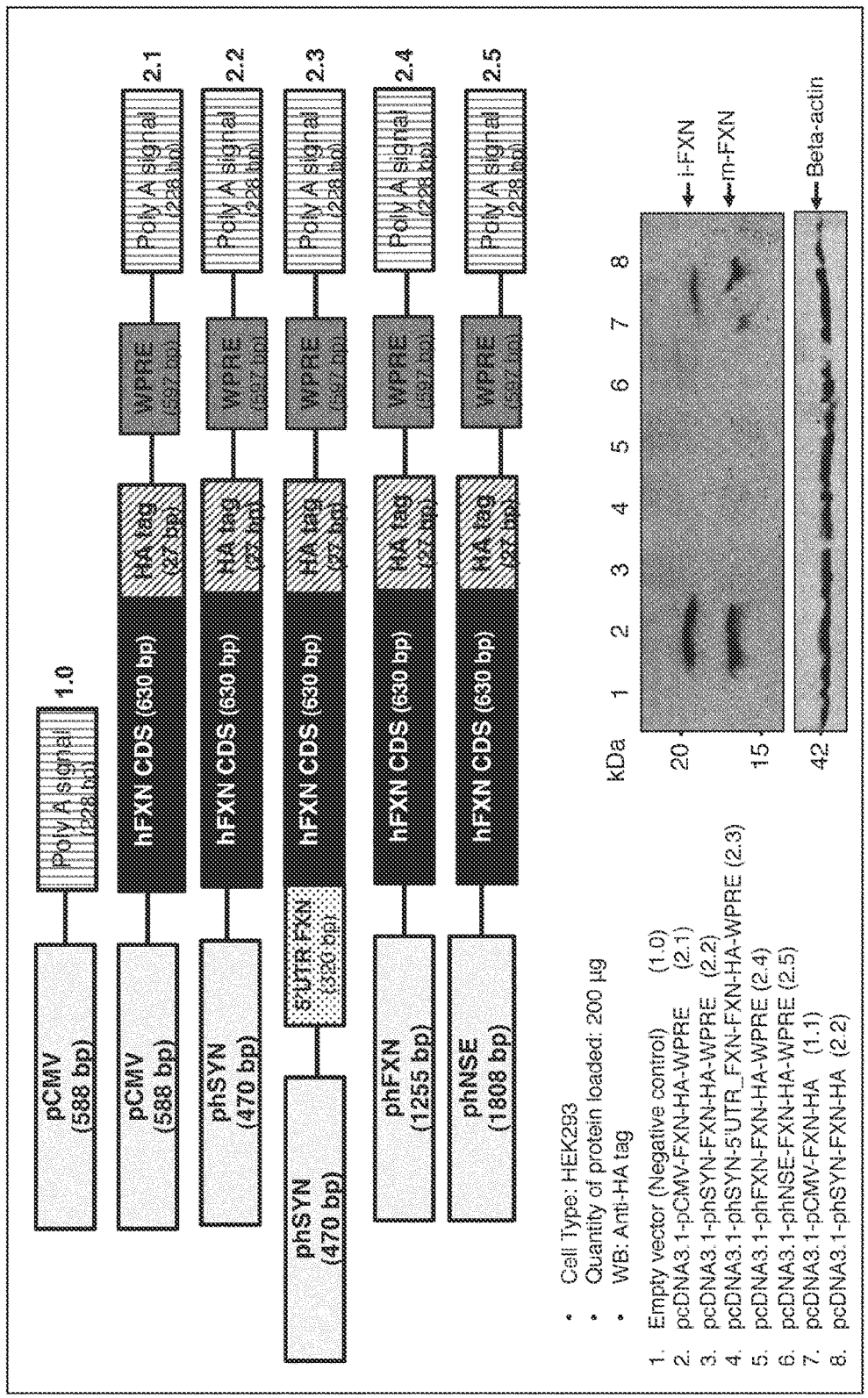

FIG. 2. Evaluation of the SYN (synapsin), NSE (neuron-specific enolase), and FXN (frataxin; 1,255 bp) human promoters together with the WPRE sequence on frataxin (FXN) protein expression. The effect of a 320 bp fragment of the 5'end from FXN, and WPRE sequences on the expression of FXN from the phSYN promoter previously shown in FIG. 1 (lane 3, 4 vs 8) and of phNSE (lane 6) was evaluated. The different constructs were transfected into HEK cells and the lysates analysed 48 hrs after transfection. The efficiency of the WPRE sequences in the stabilization of RNA is seen in the construct expressing FXN from the CMV promoter (lane 2). However, the addition and combination of the regulatory elements shown above did not result in the expression of FXN from the phSYN, hpFXN, or phNSE. HA, hemagglutinin tag; iFXN, intermediate form FXN; mFXN, mature form FXN; WPRE, woodchuck hepatitis virus posttranscriptional regulatory element.

FIG. 3. Evaluation of the SYN (synapsin), NSE (neuron-specific enolase), and FXN (frataxin; 1,255 bp) human promoters together with the CMV enhancer and WPRE sequences on frataxin (FXN) protein expression. HEK and mouse neuroblastoma cells N2a were transfected with constructs comprising the CMV enhancer together with either SYN, NSE or FXN (1,255 bp) promoters. The combination of the regulatory elements shown above did not result in the expression of FXN from the phSYN, phFXN, or phNSE promoters. HA, hemagglutinin tag; iFXN, intermediate form FXN; mFXN, mature form FXN; WPRE, woodchuck hepatitis virus posttranscriptional regulatory element.

Figure 4:
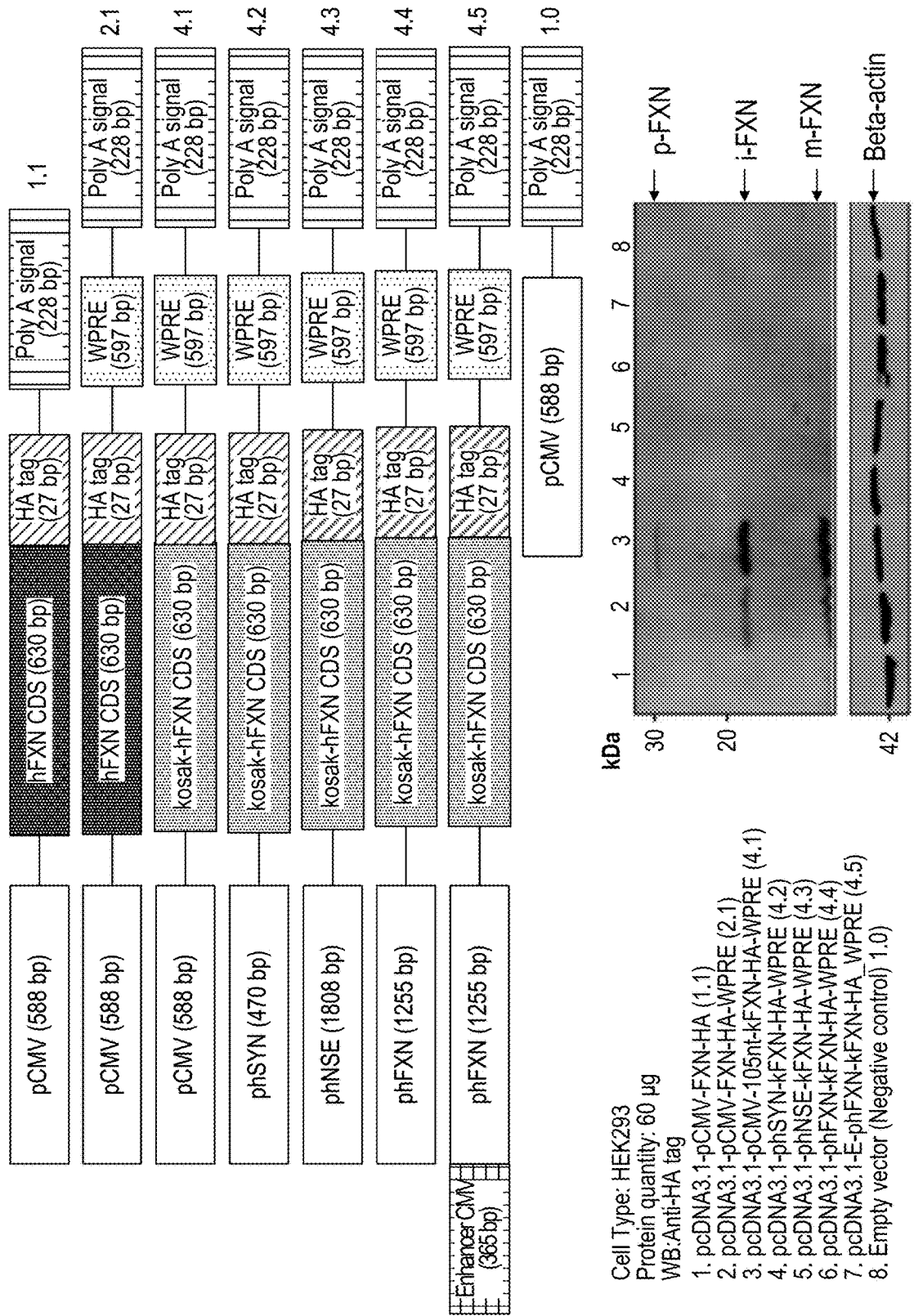

FIG. 4. Evaluation of the effect of the human promoters SYN (synapsin), NSE (neuron-specific enolase), and FXN (frataxin; 1,255 bp) human promoters with addition of the KOZAK (5') and WPRE (3') sequences on frataxin (FXN) protein expression. The different constructs were transfected into HEK cells and the lysates analysed 48 hrs after transfection. The efficiency of the WPRE sequences in the stabilization of RNA is seen in the construct expressing FXN from the CMV promoter (lane 1 vs 2). The further FXN expression enhancement by the addition of the kozak sequence and the 105 nt sequences between the promoter and the FXN coding sequence is seen in lanes 2 vs 3. However, the addition and combination of the regulatory elements shown above did not result in the expression of FXN from the phSYN, phFXN, or phNSE. HA, hemagglutinin tag; iFXN, intermediate form FXN; mFXN, mature form; pFXN, precursor form; WPRE, woodchuck hepatitis virus posttranscriptional regulatory element.

FIG. 5. Evaluation of the combination of a defined linker between the human promoters PGK1 (phosphoglycerate kinase 1), NSE (neuron-specific enolase), SYN (synapsin) or FXN (frataxin; 1,255 bp) and the coding region (CDS) of FXN in addition to the KOZAK (5') and WPRE (3') sequences on frataxin (FXN) protein expression. The different constructs shown were transfected into either N2a (A, B and E) or HEK (C and D) cells and the lysates were analysed 48 hrs after transfection. Expression of FXN was consistently detected from the phPGK, but not from the phNSE or phFXN (1,255 bp) promoter when using the 105 bp linker between the promoter and the coding region (A, C, and D: Lane 4; B: lane 5 and E: lane 8). HA, hemagglutinin tag; iFXN, intermediate form FXN; mFXN, mature form; pFXN, precursor form; WPRE, woodchuck hepatitis virus posttranscriptional regulatory element.

FIG. 6. Expression of luciferase (LUC) under the PGK1 (phosphoglycerate kinase 1) human promoter following intrathecal injection of the rAAV9 vector ($4.6 \times 10^{12}$ vg/Kg) in YG8R Tg/– and WT mice. The expression of luciferase was detected after intraperitoneal injection of 150 μls of D-luciferin at 150 mg/Kg mouse-weight 3.5 months after intrathecal injection of the vector (A). Organs were dissected and luciferase substrate was added fresh before capturing the image (relative scales shown after left and right panels (B)).

FIG. 7. In vivo expression of frataxin mRNA in 7 months-old mice intrathecally administered with rAAV9-PGK1-FXN. Frataxin mRNA levels were quantified by qRT-PCR in liver, heart, lumbar dorsal root ganglia (DRG-L), lumbar spinal cord (SC-L), thoracic spinal cord (SC-T), cervical spinal cord (SC-C), cerebellum (Cb), and brain (frontal region C1) tissues from 7-months-old YG8R hemizygous transgenic (Tg/–) or homozygous (Tg/Tg) mice. YG8R hemizygous transgenic mice (Tg/–) were administered with either rAAV-Null (shown in black) or rAAV9-PGK1-FXN (shown in light grey) and the FRDA homozygous transgenic mice (Tg/Tg) (shown in dark grey) were not injected. Unlike the YG8R hemizygous mice (Tg/–) carrying two tandem copies of the human FXN gene with ~82 and ~190 GAA trinucleotide sequence repeats in one of the chromosomes, the homozygous YG8R mice contain the two tandem copies in each of the chromosomes. Neither the homozygous or the hemizygous YG8R mice for the human FXN express endogenous Fxn since they have a mouse Fxn knockout genetic background. The homozygous YG8R mice served as a higher expressing control for the human FXN mRNA since it contains more copies of the human transgene yet exhibiting normal functions. Mice were injected intrathecally at 2.5 months of age and human FXN-specific primers were used to quantify FXN mRNA in the different tissues. Levels of total FXN mRNA were normalized to levels of those detected in the YG8R hemizygous mice (Tg/–) treated with rAAV9-Null for each of the tissues analysed. Five months after intrathecal injection of the rAAV9-PGK1-FXN vector, the levels of the FXN mRNA were higher (around 1.3 and 3.2-fold) in the rAAV9-PGK1-FXN injected hemizygous YG8R mice (Tg/–) with the dosage tested but not higher than levels in the homozygous YG8R mice (Tg/Tg) which in all tissues, compared with the levels in Tg/– mice AAV-Null treated. A) Relative levels of human FXN mRNA in both females and males mice n=6 (3 females and 3 males). Fold differences between Friedreich ataxia mice model YG8R mice injected with the control AAV-null compared to the rAAV9-PGK1-FXN injected YG8R mice are statistically significant in liver, dorsal root ganglia and spinal cord ($p=0.019$, $p=0.004$, and $p=0.024$; denoted by asterisk *) with increasing trends in all other tissues shown. More variability was observed in male compared to female mice with the dose used. B) Relative levels of hFXN mRNA in female YG8R mice. Statistically significant fold differences in frataxin levels are detected in all tissues studied as denoted by asterisk and listed in the table below. The fold increases in the rAAV9-PGK1-FXN injected mice were never higher than levels detected in the Tg/Tg YG8R mice. Statistical significance, $p<0.05$*, $p<0.005$**

Figure 8:
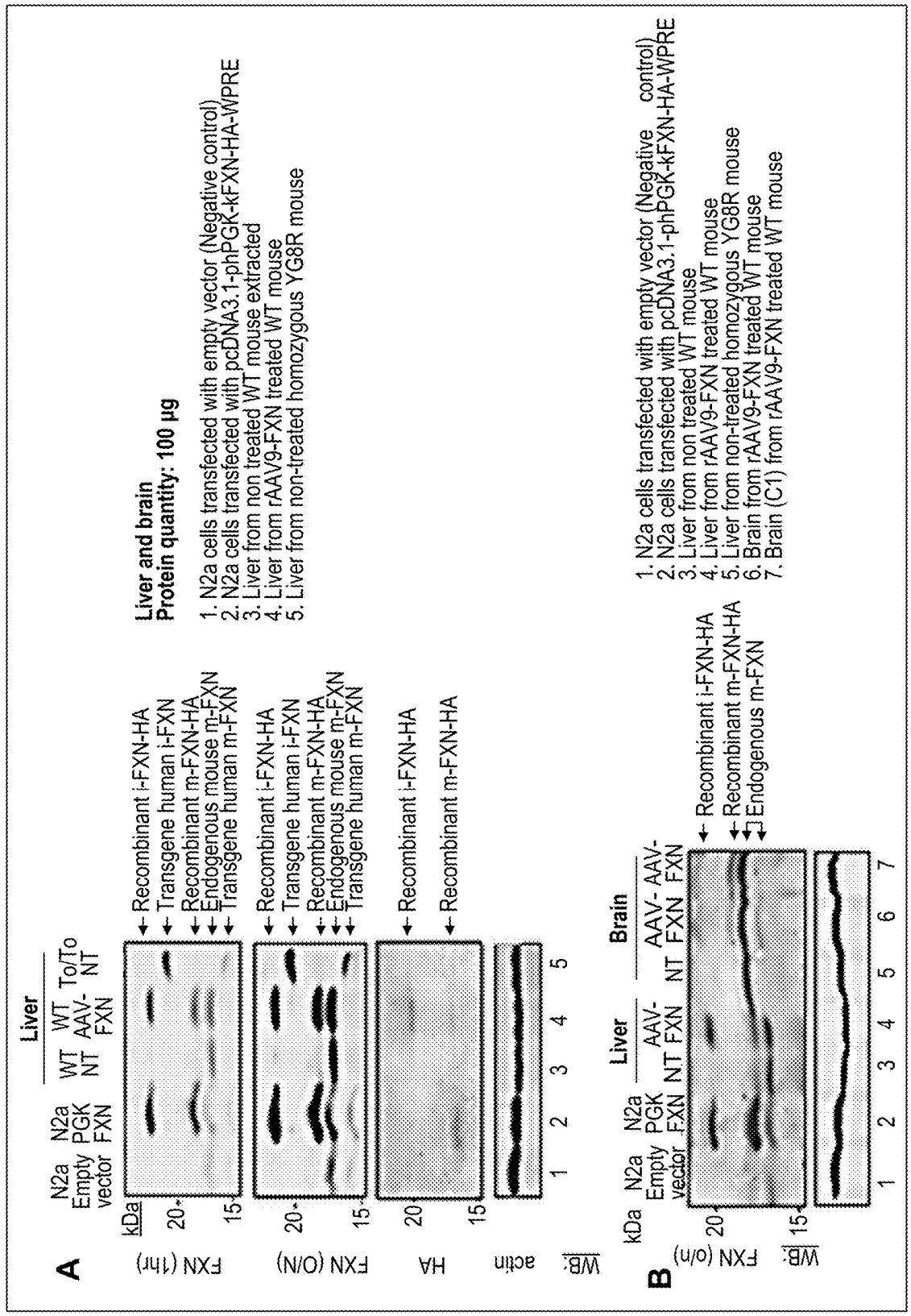

FIG. 8. In vivo expression of the recombinant frataxin protein from the rAAV9-hPGK1-FXN vector after intrathecal injection. Lysates from cultured cells N2a transfected with empty vector or the frataxin expressing vector which was used as a positive control (FIGS. 8A and 8B: lanes 1 and 2). The endogenous FXN protein in the N2a cells and WT mice are detected with the anti-FXN antibody (A and B). The human FXN protein from the transgene in the YG8R mice as well as the human recombinant FXN protein in the injected mice are detected in both the liver and the mice brain (A and B). Incubation of the blots with the anti-FXN antibody for one hour begins to reveal the human FXN protein while overnight (o/n) incubation reveals both the mouse FXN in the WT mice, and the human FXN in the hemizygous (Tg/–) and homozygous mice (Tg/Tg). Levels of expression of the recombinant human FXN protein expressed from the injected rAAV9-FXN are similar to the levels of the endogenous mouse FXN protein in the WT mice. HA, hemagglutinin tag; iFXN, intermediate form FXN; mFXN, mature form FXN; WPRE, woodchuck hepatitis virus posttranscriptional regulatory element.

Figure 9:
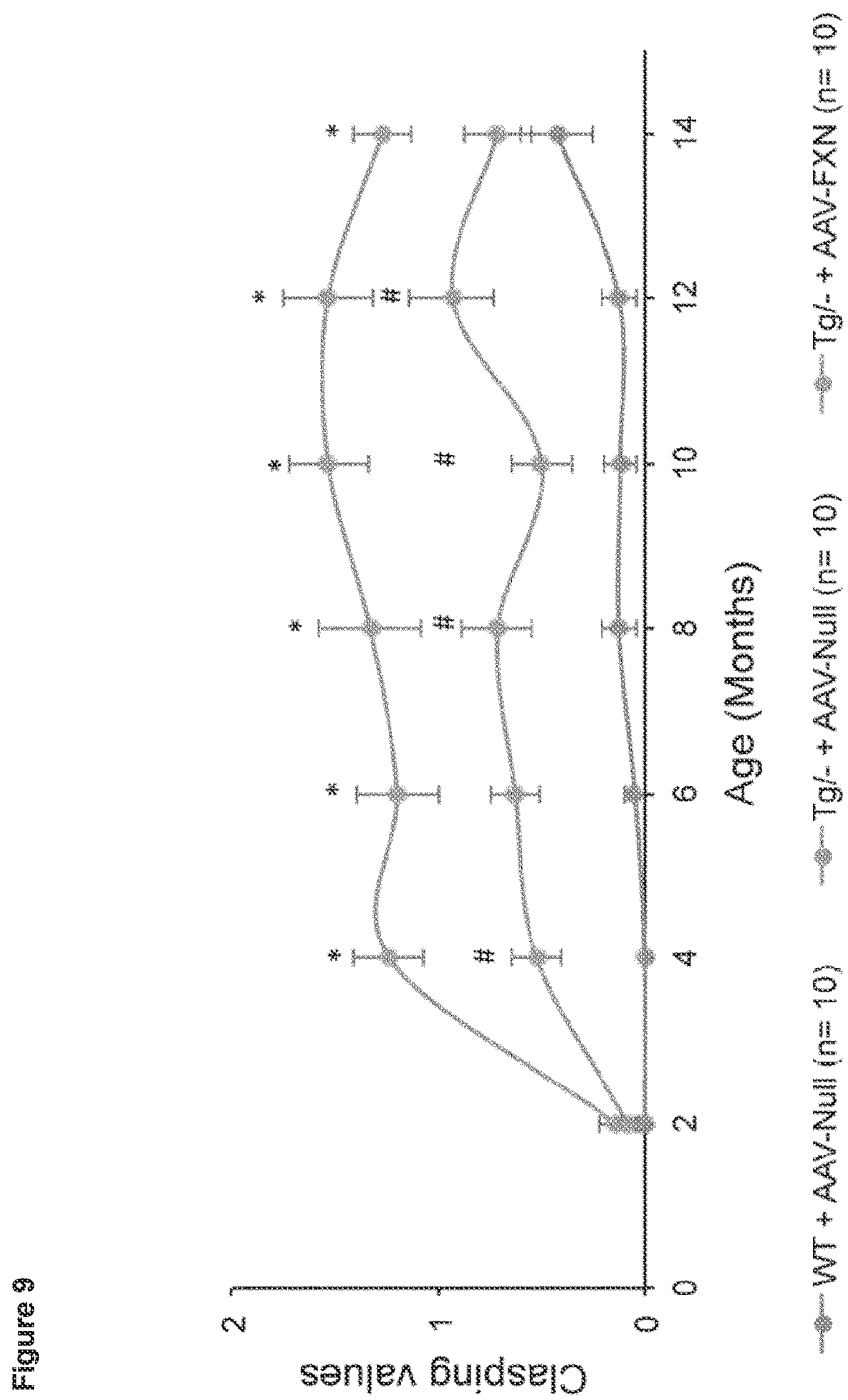

FIG. 9. Restoration of the clasping reflex in the YG8R mice over time following injection with the rAAV9-FXN vector. Clasping of hindlimbs was scored from 0 to 3 (see Methods), denoting less to more impairment, in hemizygous (Tg/–) mice and WT injected with rAAV9-FXN or rAAV9-null vectors. Results for females and males together (n=10, 5 males and 5 females for each group). Alterations in the clasping reflex are detected as early as 4 months of age in the hemizygous YG8R mice. Following intrathecal injection of the rAAV9-FXN vector the clasping reflex appears to normalize, indicating a restoration over time of this neurological pathological phenotype. Asterisks (*) denote significant differences between values for WT and the Tg/– mice injected with rAAV9-null and the pound signs (#) denotes significant differences between values obtained for the Tg/– mice injected with rAAV9-null and Tg/– mice injected with rAAV9-FXN. *, #: $P<0.05$ FIG. 10. In vivo expression of recombinant frataxin protein in the rAAV9-hPGK1-FXN injected mice restores the electrophysiological properties at the different distances from the stimulus (D1-D4) of the caudal nerve. Asterisks (*) denote significant differences between WT and Tg/− YG8R FRDA mice treated with rAAV9-null, while the pound (#) sign denotes significant differences between the rAAV9-null and the rAAV9-FXN YG8R-treated mice. Intrathecal injection of the mice at 2.5 months of age with the rAAV9-FXN vector prevents or slows the defects in nerve conduction in the FRDA mouse model for FRDA (YG8R). WT, green (n=10); Tg/− YG8R FRDA mice treated with the rAAV9-null vector, grey (n=10); Tg/− YG8R FRDA mice treated with the rAAV9-FXN vector, blue (n=10). Measurements were obtained at 1 cm, 2 cm, 3 cm and 4 cm from the tail tip denoted as values for sites D1, D2, D3, and D4, respectively *, #: P<0.05.

Figure 11:
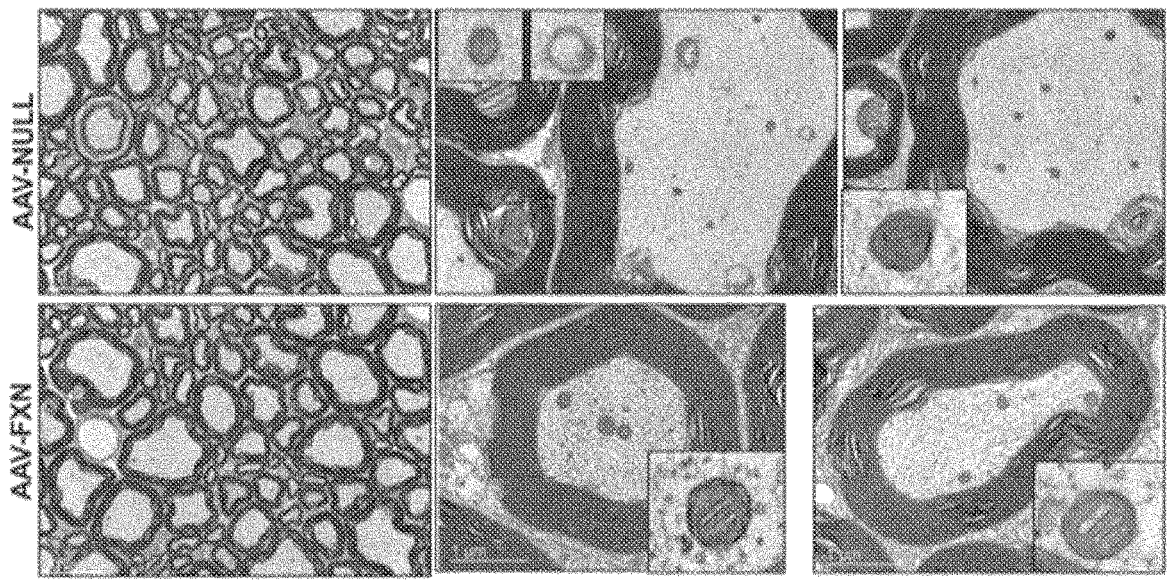

FIG. 11. Preservation of dorsal root ganglia in the rAAV9-FXN treated FRDA mouse model YG8R mice. The caliber of the dorsal root ganglia lumbar appeared preserved as well as the mitochondria morphology in the FRDA mouse model treated with the rAAV9-FXN compared with the same mice treated with the rAAV9-null virus.

SUMMARY OF THE INVENTION

The present invention provides an adeno-associated virus (AAV) vector comprising a nucleic acid, wherein the nucleic acid comprises: (i) a nucleic acid sequence encoding frataxin; (ii) a phospho-glycerate-kinase (PGK) promoter; and (iii) a woodchuck hepatitis virus posttranscriptional regulatory element (WPRE). The present invention also provides a nucleic acid comprising: (i) a nucleic acid sequence encoding frataxin; (ii) a PGK promoter; and (iii) a WPRE; a cloning vector which comprises the nucleic acid and a transfer vector which comprises the nucleic acid. Further, the present invention encompasses the use of the nucleic acid, cloning vector or transfer vector for the production of the AAV vector of the present invention. Also, the present invention provides a pharmaceutical composition and the use of the AAV vector, nucleic acid or pharmaceutical composition as a medicament, specifically as a medicament for the treatment of FRDA.

DETAILED DESCRIPTION OF THE INVENTION

Definitions

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

The term "therapeutically effective amount" refers to an amount of matter which has a therapeutic effect and which is able to treat FRDA.

The terms "individual", "patient" or "subject" are used interchangeably in the present application and are not meant to be limiting in any way. The "individual", "patient" or "subject" can be of any age, sex and physical condition.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulphur containing reducing agents, such as urea, glutathione, thioctic acid, sodium thioglycolate, thioglycerol, [alpha]-monothioglycerol, and sodium thio sulphate; low molecular weight proteins, such as human serum albumin, bovine serum albumin, gelatin, or other immunoglobulins; and hydrophilic polymers, such as polyvinylpyrrolidone.

The term "frataxin" refers to a protein which is encoded by the FXN gene and which is usually localized in the mitochondrion. Details of the protein can be found in the UniProtKB database under accession number Q16595.

The term "promoter" refers to a DNA sequence to which RNA polymerase can bind to in order to initiate transcription. The sequence may further contain binding sites for various proteins that regulate transcription, such as transcription factors. The promoter sequence may be composed of different promoter fragments (either different or the same fragments) that are localized closely in the DNA sequence and may be separated by linkers or spacers. Such promoters are referred to as chimeric promoters. In a preferred embodiment, the term "promoter" refers to a phospho-glycerate-kinase (PGK) promoter.

The term "posttranscriptional regulatory element" refers to a DNA sequence that when transcribed creates a tertiary structure which enhances or inhibits the expression of a protein.

The term "operably linked" refers to two or more nucleic acid sequences that are connected in a way that allows one nucleic acid sequence to influence another. For example, the PGK promoter and the WPRE are operably linked to the nucleic acid sequence encoding frataxin so that the expression levels of frataxin are regulated by the PGK promoter and WPRE.

The term "functional variant" refers to nucleic or amino acids whose nucleic or amino acid sequence differs in one or more positions from the parental nucleic or amino acid sequence, whereby differences might be additions, deletions and/or substitutions of nucleic acids or amino acid residues, and which are still functional and therefore a suitable for treating FRDA. A skilled person may determine functional variants by seeking homologues with a BLAST search or by studying the variability of the protein or gene in a population.

The term "Adeno-associated virus" refers to a small virus which infects humans and some other primate species. A "vector" is any vehicle which can be used to artificially carry foreign genetic material into a cell. Thus, an "AAV vector" refers to a recombinant AAV which carries a nucleic acid into a cell.

AAV Vector

In a first aspect, the present invention provides an adeno-associated virus (AAV) vector comprising a nucleic acid, wherein the nucleic acid comprises: (i) a nucleic acid sequence encoding frataxin; (ii) a phospho-glycerate-kinase (PGK) promoter; and (iii) a woodchuck hepatitis virus posttranscriptional regulatory element (WPRE); wherein (ii) and (iii) are operably linked to and regulate the expression of (i).

```
SEQ ID NO: 1 refers to the following sequence:
GAATTCCGGGGTTGGGGTTGCGCCTTTTCCAAGGCAGCCCTGGGTCTGCG

CAGGGACGCGGCTGCTCTGGGCGTGGTTCCGGGAAACGCAGCGGCGCCGA

CCCTGGGTCTCGCACATTCTTCACGTCCGTTCGCAGCGTCACCCGGATCT

TCGCCGCTACCCTTGTGGGCCCCCCGGCGACGCTTCCTGCTCCGCCCTA

AGTCGGGAAGGTTCCTTGCGGTTCGCGGCGTGCCGGACGTGACAAACGGA

AGCCGCACGTCTCACTAGTACCCTCGCAGACGGACAGCGCCAGGGAGCAA

TGGCAGCGCGCCGACCGCGATGGGCTGTGGCCAATAGCGGCTGCTCAGCA

GGGCGCGCCGAGAGCAGCGGCCGGGAAGGGGCGGTGCGGGAGGCGGGGTG

TGGGGCGGTAGTGTGGGCCCTGTTCCTGCCCGCGCGGTGTTCCGCATTCT

GCAAGCCTCCGGAGCGCACGTCGGCAGTCGGCTCCCTCGTTGACCGAATC

ACCGACCTCTCTCCCCAG
```

In a preferred embodiment, the PGK promoter comprises SEQ ID NO: 1 or a sequence which is at least 75% identical to SEQ ID NO: 1. Preferably the PGK promoter comprises SEQ ID NO: 1 or a sequence which is at least 75%, 80%, 85%, 89%, 90%, 91%, 92%, 95%, 97%, 98% or 99% identical to SEQ ID NO: 1. More preferably, the PGK promoter is SEQ ID NO: 1 or a sequence which is at least 75%, 80%, 85%, 89%, 90%, 91%, 92%, 95%, 97%, 98% or 99% identical to SEQ ID NO: 1.

The sequence identity between two sequences can be determined through conventional methods. For example, by using standard alignment logarithms known in the state of the art such as BLAST (Altschul et al., 1990. J Mol Biol. 215(3): 403-10). In a preferred embodiment, the sequence identity between two sequences is determined using BLAST.

```
SEQ ID NO: 2 refers to the following sequence:
TCGACAATCAACCTCTGGATTACAAAATTTGTGAAAGATTGACTGGTATT

CTTAACTATGTTGCTCCTTTTACGCTATGTGGATACGCTGCTTTAATGCC

TTTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAGG

CAACGTGGCGTGGTGTGCACTGTGTTTGCTGACGCAACCCCCACTGGTTG

GGGCATTGCCACCACCTGTCAGCTCCTTTCCGGGACTTTCGCTTTCCCCC

TCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAA
```

```
GCTGACGTCCTTTCCATGGCTGCTCGCCTGTGTTGCCACCTGGATTCTGC

GCGGGACGTCCTTCTGCTACGTCCCTTCGGCCCTCAATCCAGCGGACCTT

CCTTCCCGCGGCCTGCTGCCGGCTCTGCGGCCTCTTCCGCGTCTTCGCCT

TCGCCCTCAGACGAGTCGGATCTCCCTTTGGGCCGCCTCCCCGCCTG
```

In a preferred embodiment, the WPRE comprises SEQ ID NO: 2 or a sequence which is at least 75% identical to SEQ ID NO: 2. Preferably WPRE comprises SEQ ID NO: 2 or a sequence which is at least 75%, 80%, 85%, 89%, 90%, 91%, 92%, 95%, 97%, 98% or 99% identical to SEQ ID NO: 2. More preferably, the WPRE is SEQ ID NO: 2 or a sequence which is at least 75%, 80%, 85%, 89%, 90%, 91%, 92%, 95%, 97%, 98% or 99% identical to SEQ ID NO: 2.

```
SEQ ID NO: 3 refers to the following sequence:
ATGTGGACTCTCGGGCGCCGCGCAGTAGCCGGCCTCCTGGCGTCACCCAG

CCCGGCCCAGGCCCAGACCCTCACCCGGGTCCCGCGGCCGGCAGAGTTGG

CCCCACTCTGCGGCCGCCGTGGCCTGCGCACCGACATCGATGCGACCTGC

ACGCCCCGCCGCGCAAGTTCGAACCAGAGAGGTCTCAACCAGATTTGGAA

TGTCAAAAAGCAGAGTGTCTATTTGATGAATTTGAGGAAATCTGGAACTT

TGGGCCACCCAGGCTCTCTAGATGAGACCACCTATGAAAGACTAGCAGAG

AGGAAACGCTGGACTCTTTAGCAGAGTTTTTTGAAGACCTTGCAGACAAG

CCATACACGTTTGAGGACTATGATGTCTCCTTTGGGAGTGGTGTCTTAAC

TGTCAAACTGGGTGGAGATCTAGGAACCTATGTGATCAACAAGCAGACGC

CAAACAAGCAAATCTGGCTATCTTCTCCATCCAGTGGACCTAAGCGTTAT

GACTGGACTGGGAAAACTGGGTGTACTCCCACGACGGCGTGTCCCTCCAT

GAGCTGCTGGCCGCAGAGCTCACTAAAGCCTTAAAAACCAAACTGGACTT

GTCTTCCTTGGCCTATTCCGGAAAAGATGCTT
```

In a preferred embodiment, the nucleic acid sequence encoding frataxin comprises SEQ ID NO: 3 or a sequence which is at least 75% identical to SEQ ID NO: 3 and is a functional variant of frataxin. Preferably, the nucleic acid sequence encoding frataxin comprises SEQ ID NO: 3 or a sequence which is at least 75%, 80%, 85%, 89%, 90%, 91%, 92%, 95%, 97%, 98% or 99% identical to SEQ ID NO: 3. More preferably, the nucleic acid sequence encoding frataxin is SEQ ID NO: 3 or a sequence which is at least 75%, 80%, 85%, 89%, 90%, 91%, 92%, 95%, 97%, 98% or 99% identical to SEQ ID NO: 3.

In a preferred embodiment, the nucleic acid further comprises: a linker between the promoter and the nucleic acid sequence encoding frataxin, wherein the linker consists of or comprises SEQ ID NO: 6 or a sequence which is at least 75% identical to SEQ ID NO: 6. Preferably, the linker consists of or comprises SEQ ID NO: 6 or a sequence which is at least 75%, 80%, 85%, 89%, 90%, 91%, 92%, 95%, 97%, 98% or 99% identical to SEQ ID NO: 6.

```
SEQ ID NO: 6 refers to the following sequence:
TGGCTAACTAGAGAACCCACTGCTTACTGGCTTATCGAAATTAATACGA

CTCACTATAGGGAGACCCAAGCTGGCTAGCGTTTAAACTTAAGCTTGGC

CGCCACC
```

In a preferred embodiment, the nucleic acid further comprises a kozak sequence and the kozak sequence is also operably linked to and regulates the expression of the nucleic acid sequence encoding frataxin. A kozak sequence is a sequence which occurs in eukaryotic mRNA and has the consensus sequence gccRccAUGG, wherein R is a purine, lower-case letters denote the most common base at a position where the base can nevertheless vary and upper-case letters are highly conserved.

SEQ ID NO: 4 refers to the following sequence:
GAATTCCGGGGTTGGGGTTGCGCCTTTTCCAAGGCAGCCCTGGGTCTGC

GCAGGGACGCGGCTGCTCTGGGCGTGGTTCCGGGAAACGCAGCGGCGCC

GACCCTGGGTCTCGCACATTCTTCACGTCCGTTCGCAGCGTCACCCGGA

TCTTCGCCGCTACCCTTGTGGGCCCCCGGCGACGCTTCCTGCTCCGCC

CCTAAGTCGGGAAGGTTCCTTGCGGTTCGCGGCGTGCCGGACGTGACAA

ACGGAAGCCGCACGTCTCACTAGTACCCTCGCAGACGGACAGCGCCAGG

GAGCAATGGCAGCGCGCCGACCGCGATGGGCTGTGGCCAATAGCGGCTG

CTCAGCAGGGCGCGCCGAGAGCAGCGGCCGGGAAGGGGCGGTGCGGGAG

GCGGGGTGTGGGCGGTAGTGTGGGCCCTGTTCCTGCCCGCGCGGTGTT

CCGCATTCTGCAAGCCTCCGGAGCGCACGTCGGCAGTCGGCTCCCTCGT

TGACCGAATCACCGACCTCTCTCCCCAGTGGCTAACTAGAGAACCCACT

GCTTACTGGCTTATCGAAATTAATACGACTCACTATAGGGAGACCCAAG

CTGGCTAGCGTTTAAACTTAAGCTTGGCCGCCACCATGTGGACTCTCGG

GCGCCGCGCAGTAGCCGGCCTCCTGGCGTCACCCAGCCCGGCCCAGGCC

CAGACCCTCACCCGGGTCCCGCGGCCGGCAGAGTTGGCCCCACTCTGCG

GCCGCCGTGGCCTGCGCACCGACATCGATGCGACCTGCACGCCCCGCCG

CGCAAGTTCGAACCAGAGAGGTCTCAACCAGATTTGGAATGTCAAAAAG

CAGAGTGTCTATTTGATGAATTTGAGGAAATCTGGAACTTTGGGCCACC

CAGGCTCTCTAGATGAGACCACCTATGAAAGACTAGCAGAGGAAACGCT

GGACTCTTTAGCAGAGTTTTTTGAAGACCTTGCAGACAAGCCATACACG

TTTGAGGACTATGATGTCTCCTTTGGGAGTGGTGTCTTAACTGTCAAAC

TGGGTGGAGATCTAGGAACCTATGTGATCAACAAGCAGACGCCAAACAA

GCAAATCTGGCTATCTTCTCCATCCAGTGGACCTAAGCGTTATGACTGG

ACTGGGAAAAACTGGGTGTACTCCCACGACGGCGTGTCCCTCCATGAGC

TGCTGGCCGCAGAGCTCACTAAAGCCTTAAAAACCAAACTGGACTTGTC

TTCCTTGGCCTATTCCGGAAAAGATGCTTTGCCCACCTAGGGATCGGAT

CCCCGGGTACCGAGCTCGAATTCTGCAGATATCCAGCACACTTTGCCTT

TCTCTCCACAGGTGTCGACAATCAACCTCTGGATTACAAAATTTGTGAA

AGATTGACTGGTATTCTTAACTATGTTGCTCCTTTTACGCTATGTGGAT

ACGCTGCTTTAATGCCTTTGTATCATGCTATTGCTTCCCGTATGGCTTT

CATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTG

ACGCAACCCCCACTGGTTGGGGCATTGCCACCACCTGTCAGCTCCTTTC

CGGGACTTTCGCTTTCCCCCTCCCTATTGCCACGGCGGAACTCATCGCC

GCCTGCCTTGCCCGCTGCTGGACAGGGGCTCGGCTGTTGGGCACTGACA

ATTCCGTGGTGTTGTCGGGGAAGCTGACGTCCTTTCCATGGCTGCTCGC

CTGTGTTGCCACCTGGATTCTGCGCGGGACGTCCTTCTGCTACGTCCCT

TCGGCCCTCAATCCAGCGGACCTTCCTTCCCGCGGCCTGCTGCCGGCTC

TGCGGCCTCTTCCGCGTCTTCGCCTTCGCCCTCAGACGAGTCGGATCTC

CCTTTGGGCCGCCTCCCCGCCTG

In a preferred embodiment, the sequence of the nucleic acid which comprises (i), (ii) and (iii) is SEQ ID NO: 4 or a sequence which is at least 75% identical to SEQ ID NO: 4. Preferably, the nucleic acid which comprises (i), (ii) and (iii) is SEQ ID NO: 4 or a sequence which is at least 75%, 80%, 85%, 89%, 90%, 91%, 92%, 95%, 97%, 98% or 99% identical to SEQ ID NO: 4.

In a preferred embodiment, the nucleic acid further comprises a PolyA signal. Preferably, the PolyA signal is at least 50, 100, 150 or 228 bp long. More preferably the PolyA signal is at least 228 bp long. Most preferably, the PolyA signal is 228 bp long.

In a preferred embodiment, the nucleic acid further comprises one or more inverted terminal repeat (ITR) sequences. Preferably the nucleic acid comprises two ITR sequences. More preferably, the ITR sequences flank the rest of the components of the nucleic acid.

SEQ ID NO: 5 refers to the following sequence:
CTGGCGCGCTCGCTCGCTCACTGAGGCCGCCCGGGCAAAGCCCGGGCGT

CGGGCGACCTTTGGTCGCCCGGCCTCAGTGAGCGAGCGAGCGCGCAGAG

AGGGAGTGGCCAACTCCATCACTAGGGGTTCCTGAATTCCGGGGTTGGG

GTTGCGCCTTTTCCAAGGCAGCCCTGGGTCTGCGCAGGGACGCGGCTGC

TCTGGGCGTGGTTCCGGGAAACGCAGCGGCGCCGACCCTGGGTCTCGCA

CATTCTTCACGTCCGTTCGCAGCGTCACCCGGATCTTCGCCGCTACCCT

TGTGGGCCCCCGGCGACGCTTCCTGCTCCGCCCCTAAGTCGGGAAGGT

TCCTTGCGGTTCGCGGCGTGCCGGACGTGACAAACGGAAGCCGCACGTC

TCACTAGTACCCTCGCAGACGGACAGCGCCAGGGAGCAATGGCAGCGCG

CCGACCGCGATGGGCTGTGGCCAATAGCGGCTGCTCAGCAGGGCGCGCC

GAGAGCAGCGGCCGGGAAGGGGCGGTGCGGGAGGCGGGGTGTGGGCGG

TAGTGTGGGCCCTGTTCCTGCCCGCGCGGTGTTCCGCATTCTGCAAGCC

TCCGGAGCGCACGTCGGCAGTCGGCTCCCTCGTTGACCGAATCACCGAC

CTCTCTCCCCAGTGGCTAACTAGAGAACCCACTGCTTACTGGCTTATCG

AAATTAATACGACTCACTATAGGGAGACCCAAGCTGGCTAGCGTTTAAA

CTTAAGCTTGGCCGCCACCATGTGGACTCTCGGGCGCCGCGCAGTAGCC

GGCCTCCTGGCGTCACCCAGCCCGGCCCAGGCCCAGACCCTCACCCGGG

TCCCGCGGCCGGCAGAGTTGGCCCCACTCTGCGGCCGCCGTGGCCTGCG

CACCGACATCGATGCGACCTGCACGCCCCGCCGCGCAAGTTCGAACCAG

AGAGGTCTCAACCAGATTTGGAATGTCAAAAAGCAGAGTGTCTATTTGA

TGAATTTGAGGAAATCTGGAACTTTGGGCCACCCAGGCTCTCTAGATGA

GACCACCTATGAAAGACTAGCAGAGGAAACGCTGGACTCTTTAGCAGAG

-continued
TTTTTTGAAGACCTTGCAGACAAGCCATACACGTTTGAGGACTATGATG

TCTCCTTTGGGAGTGGTGTCTTAACTGTCAAACTGGGTGGAGATCTAGG

AACCTATGTGATCAACAAGCAGACGCCAAACAAGCAAATCTGGCTATCT

TCTCCATCCAGTGGACCTAAGCGTTATGACTGGACTGGGAAAAACTGGG

TGTACTCCCACGACGGCGTGTCCCTCCATGAGCTGCTGGCCGCAGAGCT

CACTAAAGCCTTAAAAACCAAACTGGACTTGTCTTCCTTGGCCTATTCC

GGAAAAGATGCTTTGCCCACCTAGGGATCGGATCCCCGGGTACCGAGCT

CGAATTCTGCAGATATCCAGCACACTTTGCCTTTCTCTCCACAGGTGTC

GACAATCAACCTCTGGATTACAAAATTTGTGAAAGATTGACTGGTATTC

TTAACTATGTTGCTCCTTTTACGCTATGTGGATACGCTGCTTTAATGCC

TTTGTATCATGCTATTGCTTCCCGTATGGCTTTCATTTTCTCCTCCTTG

TATAAATCCTGGTTGCTGTCTCTTTATGAGGAGTTGTGGCCCGTTGTCA

GGCAACGTGGCGTGGTGTGCACTGTGTTTGCTGACGCAACCCCCACTGG

TTGGGGCATTGCCACCACCTGTCAGCTCCTTTCCGGGACTTTCGCTTTC

CCCCTCCCTATTGCCACGGCGGAACTCATCGCCGCCTGCCTTGCCCGCT

GCTGGACAGGGGCTCGGCTGTTGGGCACTGACAATTCCGTGGTGTTGTC

GGGGAAGCTGACGTCCTTTCCATGGCTGCTCGCCTGTGTTGCCACCTGG

ATTCTGCGCGGGACGTCCTTCTGCTACGTCCCTTCGGCCCTCAATCCAG

CGGACCTTCCTTCCCGCGGCCTGCTGCCGGCTCTGCGGCCTCTTCCGCG

TCTTCGCCTTCGCCCTCAGACGAGTCGGATCTCCCTTTGGGCCGCCTCC

CCGCCTGGAATTCGAGCTCGGTACGATCAGCTGATCAGCCTCGACTGTG

CCTTCTAGTTGCCAGCCATCTGTTGTTTGCCCCTCCCCCGTGCCTTCCT

TGACCCTGGAAGGTGCCACTCCCACTGTCCTTTCCTAATAAAATGAGGA

AATTGCATCGCATTGTCTGAGTAGGTGTCATTCTATTCTGGGGGGTGGG

GTGGGGCAGGACAGCAAGGGGGAGGATTGGGAAGACAATAGCAGGCATG

CTGGGGATGCGGTGGGCTCTATGGCTGGCGCGCTCGCTCGCTCACTGAG

GCCGCCCGGGCAAAGCCCGGGCGTCGGGCGACCTTTGGTCGCCCGGCCT

CAGTGAGCGAGCGAGCGCGCAGAGAGGGAGTGGCCAACTCCATCACTAG

GGGTTCCT

In a preferred embodiment, the nucleic acid is SEQ ID NO: 5 or a sequence which is at least 75% identical to SEQ ID NO: 5. Preferably, the nucleic acid is SEQ ID NO: 5 or a sequence which is at least 75%, 80%, 85%, 89%, 90%, 91%, 92%, 95%, 97%, 98% or 99% identical to SEQ ID NO: 5.

In a preferred embodiment, the vector allows for the expression of a therapeutically effective amount of frataxin in a patient who suffers from Friedreich's ataxia. Thus, the vector delivers the nucleic acid to a patient's cells where the nucleic acid then expresses frataxin at a therapeutically effective amount.

In a preferred embodiment, the AAV vector is an AAV serotype 9 vector, i.e. an AAV-9 vector.

Nucleic Acid

In a second aspect, the present invention provides a nucleic acid comprising: (i) a nucleic acid sequence encoding frataxin; (ii) a PGK promoter; and (iii) a WPRE; wherein (ii) and (iii) are operably linked to and regulate the expression of (i).

In a preferred embodiment, the PGK promoter comprises SEQ ID NO: 1 or a sequence which is at least 75% identical to SEQ ID NO: 1. Preferably the PGK promoter comprises SEQ ID NO: 1 or a sequence which is at least 75%, 80%, 85%, 89%, 90%, 91%, 92%, 95%, 97%, 98% or 99% identical to SEQ ID NO: 1. More preferably, the PGK promoter is SEQ ID NO: 1 or a sequence which is at least 75%, 80%, 85%, 89%, 90%, 91%, 92%, 95%, 97%, 98% or 99% identical to SEQ ID NO: 1.

In a preferred embodiment, the WPRE comprises SEQ ID NO: 2 or a sequence which is at least 75% identical to SEQ ID NO: 2. Preferably WPRE comprises SEQ ID NO: 2 or a sequence which is at least 75%, 80%, 85%, 89%, 90%, 91%, 92%, 95%, 97%, 98% or 99% identical to SEQ ID NO: 2. More preferably, the WPRE is SEQ ID NO: 2 or a sequence which is at least 75%, 80%, 85%, 89%, 90%, 91%, 92%, 95%, 97%, 98% or 99% identical to SEQ ID NO: 2.

In a preferred embodiment, the nucleic acid sequence encoding frataxin comprises SEQ ID NO: 3 or a sequence which is at least 75% identical to SEQ ID NO: 3 and is a functional variant of frataxin. Preferably, the nucleic acid sequence encoding frataxin comprises SEQ ID NO: 3 or a sequence which is at least 75%, 80%, 85%, 89%, 90%, 91%, 92%, 95%, 97%, 98% or 99% identical to SEQ ID NO: 3. More preferably, the nucleic acid sequence encoding frataxin is SEQ ID NO: 3 or a sequence which is at least 75%, 80%, 85%, 89%, 90%, 91%, 92%, 95%, 97%, 98% or 99% identical to SEQ ID NO: 3.

In a preferred embodiment, the nucleic acid further comprises: a linker between the promoter and the nucleic acid sequence encoding frataxin, wherein the linker consists of or comprises SEQ ID NO: 6 or a sequence which is at least 75% identical to SEQ ID NO: 6. Preferably, the linker consists of or comprises SEQ ID NO: 6 or a sequence which is at least 75%, 80%, 85%, 89%, 90%, 91%, 92%, 95%, 97%, 98% or 99% identical to SEQ ID NO: 6.

In a preferred embodiment, the nucleic acid further comprises a kozak sequence and the kozak sequence is also operably linked to and regulates the expression of the nucleic acid sequence encoding frataxin.

In a preferred embodiment, the sequence of the nucleic acid which comprises (i), (ii) and (iii) is SEQ ID NO: 4 or a sequence which is at least 75% identical to SEQ ID NO: 4. Preferably, the nucleic acid which comprises (i), (ii) and (iii) is SEQ ID NO: 4 or a sequence which is at least 75%, 80%, 85%, 89%, 90%, 91%, 92%, 95%, 97%, 98% or 99% identical to SEQ ID NO: 4.

In a preferred embodiment, the nucleic acid further comprises a PolyA signal. Preferably, the PolyA signal is at least 50, 100, 150 or 228 bp long. More preferably the PolyA signal is at least 228 bp long. Most preferably, the PolyA signal is 228 bp long.

In a preferred embodiment, the nucleic acid further comprises one or more inverted terminal repeat (ITR) sequences. Preferably the nucleic acid comprises two ITR sequences. More preferably, the ITR sequences flank the rest of the components of the nucleic acid.

In a preferred embodiment, the nucleic acid is SEQ ID NO: 5 or a sequence which is at least 75% identical to SEQ ID NO: 5. Preferably, the nucleic acid is SEQ ID NO: 5 or a sequence which is at least 75%, 80%, 85%, 89%, 90%, 91%, 92%, 95%, 97%, 98% or 99% identical to SEQ ID NO: 5.

Cloning Vector

In a third aspect, the present invention provides a cloning vector which comprises the nucleic acid according to any one of the previously described embodiments and additional nucleic acid elements for promoting replication of the cloning vector in a bacterial cell.

The term "cloning vector" refers to any vector that is suitable for cloning, which generally involves the presence of restriction sites, an origin of replication for bacterial propagation and a selectable marker.

The cloning vector of the invention comprises the nucleic acid of the invention and can preferably be used to produce the transfer vector or AAV vector of the invention.

Transfer Vector

In a fourth aspect, the present invention provides a transfer vector which comprises the nucleic acid according to any one of the previously described embodiments and additional nucleic acid elements for promoting integration or transposition of the transfer vector into an AAV vector, preferably an AAV-9 vector.

The term "transfer vector" refers to a vector that is suitable for integration or transposition in an AAV vector. The transfer vector thus generally permits the insertion of genetic information into an AAV vector.

The transfer vector of the invention comprises the nucleic acid of the invention and can preferably be used to produce the AAV vector of the invention.

Use of the Nucleic Acid, Cloning Vector and Transfer Vector

In a fifth aspect, the present invention provides the use of the nucleic acid of the present invention, the cloning vector of the present invention or the transfer vector of the present invention for the production of an AAV vector according to any one of the embodiments previously described.

Pharmaceutical Composition

In a sixth aspect, the present invention provides a pharmaceutical composition comprising the AAV vector of the present invention or the nucleic acid of the present invention and a pharmaceutically acceptable carrier or diluent.

A pharmaceutical composition as described herein may also contain other substances. These substances include, but are not limited to, cryoprotectants, lyoprotectants, surfactants, bulking agents, anti-oxidants, and stabilizing agents. In some embodiments, the pharmaceutical composition may be lyophilized.

The term "cryoprotectant" as used herein, includes agents which provide stability to the AAV vector against freezing-induced stresses, by being preferentially excluded from the AAV vector's surface. Cryoprotectants may also offer protection during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

In one embodiment, a lyoprotectant is added to a pharmaceutical composition described herein. The term "lyoprotectant" as used herein, includes agents that provide stability to the AAV vector during the freeze-drying or dehydration process (primary and secondary freeze-drying cycles), by providing an amorphous glassy matrix and by binding with the AAV vector's surface through hydrogen bonding, replacing the water molecules that are removed during the drying process. This helps to minimize product degradation during the lyophilization cycle, and improve the long-term product stability. Non-limiting examples of lyoprotectants include sugars, such as sucrose or trehalose; an amino acid, such as monosodium glutamate, non-crystalline glycine or histidine; a methylamine, such as betaine; a lyotropic salt, such as magnesium sulphate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a pharmaceutical composition is generally an amount that does not lead to an unacceptable amount of degradation of the strain when the pharmaceutical composition is lyophilized.

In some embodiments, a bulking agent is included in the pharmaceutical composition. The term "bulking agent" as used herein, includes agents that provide the structure of the freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the strain stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in formulations in an amount from 0.5% to 10%.

Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulphate; low molecular weight proteins, such as human serum albumin, bovine serum albumin, gelatin, or other immunoglobulins; and hydrophilic polymers, such as polyvinylpyrrolidone.

The pharmaceutical composition may be prepared for oral, sublingual, buccal, intravenous, intramuscular, subcutaneous, intraperitoneal, conjunctival, rectal, transdermal, intrathecal, topical and/or inhalation-mediated administration. In a preferred embodiment, the pharmaceutical composition may be a solution which is suitable for intravenous, intramuscular, conjunctival, transdermal, intraperitoneal and/or subcutaneous administration. In another embodiment, the pharmaceutical composition may be a solution which is suitable for sublingual, buccal and/or inhalation-mediated administration routes. In an alternative embodiment, the pharmaceutical composition may be a gel or solution which is suitable for intrathecal administration. In an alternative embodiment, the pharmaceutical composition may be an aerosol which is suitable for inhalation-mediated administration. In a preferred embodiment, the pharmaceutical composition may be prepared for intrathecal administration.

The pharmaceutical composition may further comprise common excipients and carriers which are known in the state of the art. For solid pharmaceutical compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For solution for injection, the pharmaceutical composition may further comprise cryoprotectants, lyoprotectants, surfactants, bulking agents, anti-oxidants, stabilizing agents and pharmaceutically acceptable carriers. For aerosol administration, the pharmaceutical compositions are generally supplied in finely divided form along with a surfactant and propellant. The surfactant must, of course, be nontoxic, and is generally soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. For suppositories, traditional binders and carriers may include, for example, polyalkalene glycols or triglycerides.

Medical Uses

In a seventh aspect, the present invention provides the AAV vector of the present invention, the nucleic acid of the present invention or the pharmaceutical composition of the present invention for use as a medicament. In an eight aspect, the present invention provides the AAV vector of the present invention, the nucleic acid of the present invention or the pharmaceutical composition of the present invention for use in the treatment of Friedreich's ataxia.

In a preferred embodiment, the AAV vector of the present invention, the nucleic acid of the present invention or the pharmaceutical composition of the present invention is administered intrathecally, intramuscularly, intracerebrally or intracerebroventricularly, preferably intrathecally or intramuscularly.

In a preferred embodiment, the AAV vector of the present invention, the nucleic acid of the present invention or the pharmaceutical composition of the present invention is administered at a dose of at least $1\times10^9$ vector genomes/Kg body weight, preferably $1\times10^{10}$, $1\times10^{11}$ or $1\times10^{12}$ vector genomes/Kg body weight. More preferably, at least or about $4.6\times10^{12}$ vector genomes/Kg body weight are administered.

EXAMPLES

Example 1: Plasmid Construction

The coding sequence of the isoform 1 of human frataxin (hFXN) was fused to a hemagglutinin tag (HA) and cloned into the pcDNA3.1 expression vector using the with In-Fusion® HD Cloning Kit (Clontech). The fusion system was used for all the cloning steps. Several constructs were generated fusing either the CMV, or the human (h) promoters (p) of synapsin (phSYN), neuron-specific enolase (phNSE), 1,255 bp of the FXN promoter (phFXN1255), or the human phosphoglycerate kinase isoform 1 (phPGK1) with the coding region of the FXN gene. Further regulatory elements such as the CMV enhancer and the Kozak sequences were added at the 5 prime-end in addition to the woodchuck hepatitis virus responsive element (WPRE) sequence at the 3 prime-end. All these expression vectors generated constructs are listed in Table 2.

Plasmids containing the same combination of regulatory elements were also generated to drive luciferase expression by replacing the coding sequence of FXN for the firefly luciferase coding sequence (LUC) that was amplified from the pGL3-LUC vector (Promega) also using the In-Fusion® HD Cloning Kit (Clontech). These plasmids are listed in Table 3.

Example 2: Recombinant Adeno-Associated Viral Vector Construction and Production The expression cassettes from the pcDNA3.1-phPGK-kFXN-HA-WPRE and of the pcDNA3.1-phPGK-kLUC-HA-WPRE plasmid were cloned into the SnaBl-Mfel sites of the recombinant AAV9 vector (rAAV9-phPGK1-FXN-HA-WPRE vector and rAAV9-phPGK-LUC-WPRE vector). In addition, a control null vector was generated lacking the FXN coding sequence (AAV2/9-null). All three constructs and viral particles were generated by the Vector Production Unit at Center of Animal Biotechnology and Gene Therapy (Universitat AutOnoma de Barcelona). The final titers obtained were $1.4\times10^{13}$ vg/ml for AAV9-phPGK-FXN-HA-WPRE, $9.8\times10^{12}$ vg/ml for AAV9-phPGK-LUC-WPRE, and $6\times10^{12}$ vg/ml for AAV2/9-null.

Example 3: Optimizing Frataxin Expression

1. Cell Culture, In Vitro Expression, and Luciferase Reporter Assay

Mouse neuroblastoma cells (N2a), Human neuroblastoma cells (SH-SYSY) and Human Embryonic Kidney (HEK 293) cells were cultured in Dulbecco's Modified Eagle's medium (DMEM) containing 10% Fetal bovine serum (Sigma), 2 mM glutamine, 50 µg/ml penicillin/streptomycin (Life technologies) at 70% confluence in 10 cm culture dishes. Transfections were carried out using lipofectamine 2000 (Life technologies) for N2a and SH-SY5Y cells and calcium phosphate for HEK 293 using 4 µg plasmid DNAs alone in addition to 0.25 µg EGFP. Following the transfection, the media was replaced with fresh DMEM culture media for the HEK cells and with Neurobasal, B27 supplement, 10 µM retinoic acid, 2 mM glutamine, 50 µg/ml Penicillin/Streptomycin for the N2a and SH-SY5Y cells. Forty-eight hours after the cell culture media change the cells transfected with the expression plasmids listed in Table 2 were harvested and stored at −80° C. until further use. For luciferase reporter assay the plasmids listed in Table 3 were transfected as mentioned above and the cells were re-plated into 384 well plates and the luciferase activity determined using the dual luciferase reporter assay kit as per manufacturer instructions (Promega).

2. SDS-PAGE and Immunoblotting

Proteins were extracted from cultured cells by homogenization in RIPA lysis buffer: 10 mM Tris-HCl pH 7.4, 140 mM NaCl, 0.1% sodium deoxycholate, 1% Triton X-100, 1% SDS, 2 mM Ethylenediaminetetraacetic acid (EDTA), 25 mM sodium fluoride (NaF), 2.5 mM NaVO3 and protein inhibitor cocktail (Roche). Protein concentration was determined using the DC-BioRad protein assay (BioRad). Total protein extract were mixed with 4× Protein Sample Loading Buffer (Li-Cor Biosciences) containing 1 mM DTT and separated by electrophoresis on a 15% acrylamide gel at constant 20 mA before transfer to PVDF membranes. Primary antibodies used were anti-FXN PAC 2518 (generous gift from by Dr. Grazia Isaya, Mayo Clinic, Rochester MN), anti-FXN (1G2, Merck Millipore), anti-HA tag (clone 16612, MMS-101P, Covance) and anti-beta actin (AC15, Sigma). Infrared-dye conjugated secondary antibodies were anti-mouse IRDye-800CW and anti-Rabbit IRDye 700CW (Li-Cor Biosciences) and the immunoreactivity was detected using the Odyssey analyser software v2.1 (Li-Cor Biosciences).

3. Results

As can be seen in FIGS. 1-5 and Tables 2-3, the provision of a construct which comprises the hPGK1 promoter, linker sequences (length and content) and the WPRE allowed for the expression of frataxin in cells. The human PGK1 promoter is a metabolically regulated promoter expressed in physiologically relevant tissues thereby making a good candidate as a promoter for frataxin. However the regulatory elements or the linker sequences/length to be used to be able to express the frataxin coding sequences was not clear. By trying different combinations of elements and sequences our results show that the protein expression from the human frataxin coding sequences requires the inclusion of an operationally functional linker between the hPGK1 promoter and the FXN coding sequences since constructs containing a length of about 105 nt allow for FXN expression while linker lengths around 35 nt do not, even with the addition of the WPRE RNA stabilizer sequence. Interestingly, this linker requirement was only noted when using the hPGK1 promoter but not with other promoters tested (ie. hSYN). Further, the levels of frataxin protein from this vector are much lower than that obtained from the CMV or CAG promoter driven vectors even in the absence of WPRE sequences thereby being more comparable to endogenous levels. One of the limitations of the previous approaches is that to be able to obtain frataxin expression, high driving promoters such as CAG or CMV promoters have been used resulting in very high levels of protein expression which may cause cellular stress and override some of the protective effects. The vector presented here is able to drive the expression of frataxin protein in relevant nervous system and peripheral tissues in quantities within physiologically functional range.

TABLE 2

Summary of results. Relative levels of FXN after transfection with different constructs

| Frataxin expression plasmids | Cell type | Antibody | Immunoreactivity |
|---|---|---|---|
| 1.1 pcDNA3.1-pCMV-FXN-HA | N2A/HEK293/SHSY | Anti-HA tag Covance)/Anti-FXN 1G2 (Merck Millipore) | ++ |
| 1.2 pcDNA3.1-phSYN-FXN-HA | SHSY | Anti-HA tag (Covance) | − |
| 1.3 pcDNA3.1-phFXN-FXN-HA | HEK293/SHSY | Anti-HA tag (Covance) | − |
| 1.4 pcDNA3.1-prNSE-FXN-HA | N2A | Anti-HA tag (Covance) | − |
| 1.5 pcDNA3.1-phNSE-FXN-HA | HEK293 | Anti-HA tag (Covance) | − |
| Addition of WPRE | | | |
| 2.1 pcDNA3.1-pCMV-FXN-HA-WPRE | N2A/HEK293 | Anti-HA tag (Covance)/Anti-FXN 1G2 (Merck Millipore) | +++ |
| 2.2 pcDNA3.1-phSYN-FXN-HA-WPRE | N2A/HEK293 | Anti-HA tag (Covance) | − |
| 2.3 pcDNA3.1-phSYN-5'UTR_FXN-FXN-HA-WPRE | N2A/HEK293 | Anti-HA tag I (Covance) | − |
| 2.4 pcDNA3.1-phFXN-FXN-HA-WPRE | N2A/HEK293 | Anti-HA tag (Covance) | − |
| 2.5 pcDNA3.1 -prNSE-FXN-HA-WPRE | N2A | Anti-HA tag (Covance) | − |
| Addition of CMV enhancer | | | |
| 3.1 pcDNA3.1-E-phFXN-FXN-HA-WPRE | HEK293 | Anti-HA tag (Covance) | − |
| 3.2 pcDNA3.1-E-phFXN-FXN-HA | N2A/HEK293 | Anti-HA tag (Covance) | − |
| 3.3 pcDNA3.1-E-phSYN-FXN-HA-WPRE | N2A | Anti-HA tag (Covance) | − |
| Addition of KOZAK and WPRE sequences | | | |
| 4.1 pcDNA3.1-pCMV-105nt-kFXN-HA-WPRE | N2A/HEK293 | Anti-HA tag (Covance)/Anti-FXN 1G2 (Merck Millipore) | ++++ |
| 4.2 pcDNA3.1-phSYN-kFXN-HA-WPRE | HEK293/N2A | Anti-HA tag (Covance) | −/+ |
| 4.3 pcDNA3.1-prNSE-kFXN-HA-WPRE | HEK293/N2A | Anti-HA tag (Covance) | −/+ |
| 4.4 pcDNA3.1-phFXN-kFXN-HA-WPRE | HEK293 | Anti-HA tag (Covance) | − |
| 4.5 pcDNA3.1-E-phFXN-kFXN-HA-WPRE | HEK293 | Anti-HA tag Covance) | − |
| Use of specific linker, KOSAK and WPRE sequences | | | |
| 5.1 pcDNA3.1-phPGK-105nt-kFXN-HA-WPRE | N2a/HEK293 | Anti-HA tagI (Covance)/Anti-FXN 1G2 (Merck Millipore) | ++ |
| 5.2 pcDNA3.1-phNSE-105nt-kFXN-HA-WPRE | N2a/HEK293 | Anti-HA tag (Covance) | + |
| 5.3 pcDNA3.1-phSYN-105nt-kFXN-HA-WPRE | N2a/HEK293 | Anti-HA tag (Covance) | − |
| 5.4 pcDNA3.1-phFXN-105nt-kFXN-HA-WPRE | N2A/HEK293 | Anti-HA tag (Covance) | − |

TABLE 3

Reporter assay of frataxin and PGK1 promoter constructs

| Luciferase expression plasmids | Cell type | Expression |
|---|---|---|
| pcDNA3.1-pCMV-135nt-LUC-WPRE | N2a/HEK293 | ++++ |
| pcDNA3.1-phPGK-135nt-LUC-WPRE | N2a/HEK293 | ++ |
| pcDNA3.1-E-phPGK-135nt-LUC-WPRE | N2a | ++ |
| pcDNA3.1-phFXN1255-135nt-LUC-WPRE | HEK293 | − |
| pcDNA3.1-phFXN1255-35nt-LUC-WPRE | N2a/HEK293 | − |
| pcDNA3.1-phFXN220-35nt-LUC-WPRE | N2a/HEK293 | + |
| pcDNA3.1-phFXN1255OCT-35nt-LUC-WPRE | N2a/HEK293 | − |

Example 4: In Vivo Data

1. Animals

The Friedreich Ataxia mouse model YG8R developed by Pook and colleagues (Pook et al. 2001. *Neurogenetics.* 3(4):185-93; Virmouni et al., 2014. *PLoS ONE.* 9(9): e107416) used in this study was obtained from the Jackson Laboratories Repository (Stock no. 012253). This human FXN transgenic mouse model is a knockout for the endogenous mouse frataxin gene (Fxn−/−) and contains the human FXN YAC transgene from a founder YG8 (carrying two tandem copies of the human FXN gene with approximately 82 and with 190 GAA trinucleotide sequence repeats). Mice were housed with SPF-Like conditions in NexGen Mouse IVC cages (Allentown, NJ) with a 12-h light-dark cycle and controlled negative pressure, temperature and humidity, and free access to water and an irradiated rodent chow Teklad global 18% protein (Envigo). The YG8R mouse colony was generated at The Institute for Health Science Research Germans Trias i Pujol (IGTP). Female and male hemizygous YG8R (Tg/−) and the WT C57Bl/6 mice were used in all experiments.

Mice hemizygous for the mutant human FXN gene (YG8R) were genotyped as previously reported (29,36). Briefly, the genomic DNA was extracted from the YG8R mouse tail by Maxwell® 16 Mouse Tail DNA Purification Kit (Promega). The transgene copy number was determined for each mouse using quantitative real-time PCR (qPCR) in LightCycler® 480 Instrument (Roche) using SYBR Premix Ex Taq II (Tli RNase H Plus) (Takara) and the following primers for human frataxin transgene: hFXN_Tg_FW: 5'-GAAC-TTCAAATTAGTTCCCCTTTCTTC-3' (SEQ ID NO: 7), hFXN_Tg_RV: 5'-CACAGCCAT-TCTTT-GGGTTTC-3' (SEQ ID NO: 8); and internal control Apolipoprotein B-100 isoform X1: IC_FW: 5'-CACG-TGGGCTCCAGCATT-3' (SEQ ID NO: 9), IC_RV: TCACCAGTCATTTCTGCCTTTG (SEQ ID NO: 10). The assay was performed with thermal cycling conditions: 95° C. for 5 minutes, and 40 cycles of 95° C. for 20 seconds and 60° C. for 30 seconds, 72° C. for 30 seconds and finally 1 cycle at 72° C. 2 min. Samples were assayed in triplicate for each gene of interest and levels of the transgene determined by the Ct (ΔΔCt) method. The transgene copy numbers was estimated relative to the Ct data from the control sample with a known copy number. The GAA repeat length was determined by GAA PCR amplification PCR using LA taq (Invitrogen) and the following primers: GAA-F: 5'-GGGAT-TGGTT-GCCAGTGCTT-AAAAGTTAG-3' (SEQ ID NO: 11) and GAA-R: 5'-GATCTAAGGACCATCATGG-CCACACTTGCC-3' (SEQ ID NO: 12). PCR products were resolved in 1.5% agarose gels by electrophoresis at 100 V for 3 hours and the band sizes were analysed. The number of GAA repeats were then determined by subtracting 451 bp (flanking non-repeat DNA) from the PCR product size, and dividing the remaining base pair repeat size by 3.

All animal procedures were carried out in accordance with EU and local regulations and approved by the appropriate local Ethics Committees.

2. AAV Administration

YG8R hemizygous and WT 10-weeks-old mice were anesthetized by intraperitoneal injection of ketamine (10 mg/kg of body weight; Imalgene 500; Rhône-Merieux, Lyon, France) and xylazine (1 mg/kg of body weight; Rompun; Bayer). Intrathecal administration of the AAV9-phPGK-FXN-HA-WPRE, AAV9-phPGK-LUC-WPRE, or AAV2/9-null was performed at the lumbar region. After lateral spine exposure, by paravertebral muscle dissection, viral vectors were slowly injected into the CSF through a 33-gauge needle and a Hamilton syringe between lumbar vertebrae L3 and L4. The appropriate access to the intrathecal space was confirmed by the animal's tail movement. Thereafter the muscle and skin were sutured. The quantity administered for each mouse of the different viral vectors was 4.6×10e-12 vg/Kg mouse weight.

3. Vector Bio-Distribution Using Luciferase Imaging

For in vivo evaluation, of the AAV9-phPGK-LUC-WPRE vector biodistribution, the mice were administered intrathecally with the vector at 10 weeks of age (2.5 months-old) and 3.5 months later they received a single intraperitoneal injection of D-luciferin substrate solution at 150 mg/kg of mouse weight. The mice were anesthetised 15 min after substrate administration by inhaled anaesthesia (isoflurane 4% for induction and 2% for maintenance). Anesthetized mice were maintained in the dark chamber of Perkin Elmer Ivis Lumina II (Caliper Life Sciences, Germany) to record the photon emissions. Images were analysed with the Living imaging software (Xenogen Corporation, CA, EUA) with 1 min integration time, 12.5 cm vision field. For ex-vivo evaluation, tissues and organs of mice were extracted after 15 min of substrate administration. Tissues and organs were placed into clear dishes and images were captured using the Living imaging software (Xenogen Corporation, CA, EUA) as above. Results can be seen in FIG. 6.

4. qRT-PCR

RNA was extracted from 30 mg of freshly frozen mouse tissue using the RNeasy Mini Kit (Qiagen). The RNA RIN and quantification was obtained with an Agilent 2200 TapeStation (Agilent). RNA was retrotranscribed to cDNA (25 ng/ul) using PrimeScript™ RT reagent Kit (Takara) with thermal conditions: 37° C. for 15 minutes, 85° C. for 5 seconds. The qRT-PCR was performed with cDNA from mouse tissues to test levels of frataxin expression in a multiwell plate format using the LightCycler480 instrument (Roche Diagnostics). Reaction mixtures contained a total volume of 10 μl consisting of 0.1 mM of each primer, 10 ng of cDNA and 5 μl of TaqMan Universal Master Mix II, no UNG (Thermofisher Scientific). Primer-probe for human frataxin detection were predesigned by Bio-rad (dH-saCPE5031641, Bio-rad), primers for Beta-2 microglobulin (B2m) housekeeping gene for mice samples were predesigned by IDT (Mm.PT.39a.22214835; IDT). The assay was performed with thermal cycling conditions: 50° C. for 2 minutes, 95° C. for 10 minutes, and 40 cycles of 95° C. for 15 seconds and 60° C. for 1 minute. Samples were assayed in triplicate for each gene of interest and the levels determined by the Ct ($\Delta\Delta$Ct) method. Results can be seen in FIG. 7.

5. SDS-PAGE and Immunoblotting

Proteins were extracted from mouse tissue by homogenization in RIPA lysis buffer: 10 mM Tris-HCl pH 7.4, 140 mM NaCl, 0.1% sodium deoxycholate, 1% Triton X-100, 1% SDS, 2 mM Ethylenediaminetetraacetic acid (EDTA), 25 mM sodium fluoride (NaF), 2.5 mM NaVO3 and protein inhibitor cocktail (Roche). Protein concentration was determined using the DC-BioRad protein assay (BioRad). Total protein extract were mixed with 4× Protein Sample Loading Buffer (Li-Cor Biosciences) containing 1 mM DTT and separated by electrophoresis on a 15% acrylamide gel at constant 20 mA before transfer to PVDF membranes. Primary antibodies used were anti-FXN PAC 2518 (generous gift from by Dr. Grazia lsaya, Mayo Clinic, Rochester MN), anti-FXN (1G2, Merck Millipore), anti-HA tag (clone 16612, MMS-101P, Covance) and anti-beta actin (AC15, Sigma). Infrared-dye conjugated secondary antibodies were anti-mouse IRDye-800CW and anti-Rabbit IRDye 700CW (Li-Cor Biosciences) and the immunoreactivity was detected using the Odyssey analyser software v2.1 (Li-Cor Biosciences). Results can be seen in FIG. 8.

6. Clasping

Hindlimb clasping has been shown to be a marker of disease progression in a number of mouse models of neurodegeneration. Each mouse was lifted by the tail away from any surrounding objects. The hindlimb position was observed for 10 seconds and scored as follows: If the hindlimbs were consistently splayed outward, away from the abdomen, it is assigned a score of 0. If one hindlimb was retracted toward the abdomen for more than 50% of the time suspended, it receives a score of 1. If both hindlimbs were partially retracted toward the abdomen for more than 50% of the time suspended, it receives a score of 2. If its hindlimbs were entirely retracted and touching the abdomen for more than 50% of the time suspended, it receives a score of 3. The clasping reflex was assessed every 2 months in mice from 4 months of age. Results can be seen in FIG. 9.

7. Electrophysiology

Amplitude ($\mu$V) and nerve conduction velocity (m/s) were measured in the caudal nerve of the mouse's tail. With animals under inhaled anaesthesia (isoflurane 2%), the stimulation electrode needle was situated subcutaneously at 4 different points of stimulation (1 cm, 2 cm, 3 cm, 4 cm from tail tip) while the registration needle point was fixed at 6 cm from tail tip. Values were recorded with the EMG/PE N-EP with 2 channels from Medelec Synergy apparatus (Viasys, EUA). During electrophysiological tests, the skin temperature of the animals was maintained above 32° C. The mice were assessed every 2 months from 4 months of age. Results can be seen in FIG. 10.

8. Results

We propose that the presented AAV treatment would be effective as treatment for FRDA because it can be expressed in physiologically relevant tissues, levels, shows similar processing as the endogenous protein and can significantly improve the electrophysiological properties of affected neurons and neurological symptoms in a mouse model of FRDA (YG8R). FIG. 6 shows that the luciferase gene in the AAV9 vector under the same regulatory elements than the FXN in the AAV9-hPGK1-FXN vector when injected intrathecally, is expressed throughout the spinal cord, brain as well as in peripheral tissues. Also expression of a luciferase under the same vector and regulatory elements stay consistent around at least 7 months after injection (data no shown). Because diminished levels of frataxin underlie most if not all the symptoms in FRDA and individuals carriers for the mutation expressing $\geq$25% levels of frataxin are free of FRDA symptoms, a small increase in the FXN expression should be able to prevent or significantly ameliorate symptoms in FRDA patients. However, very high levels of FXN expression or any other protein could induce cellular and eventually diminish the protective effects or even worsen the symptoms. Therefore, it is of interest to develop a FXN expressing vector that results in levels as similar as possible to those of the endogenous FXN protein. Therefore we developed a vector (AAV9-hPGK1-FXN) vector that allows for the expression of FXN under a metabolically regulated promoted in physiologically relevant levels and delivered it intrathecally into 10-week-old YG8R hemizygous mice (Tg/−). Higher levels of FXN mRNA were detected in the YG8R hemizygous mice (Tg/−) 3.5 months after intrathecal injection of the AAV9-PGK1-FXN vector compared to non-injected mice both in the liver and thoracic portion of the spinal cord (0.5 and 2-fold, respectively; FIG. 7). These were equal or lower than in the homozygous YG8R mice which showed 0.5 and 3-fold spinal cord, respectively compared to the hemizygous YG8R mice. This indicates that this FXN encoding vector injected in the L3-L4 intrathecal region was taken-up and expressed in thoracic spinal cord neurons by either retrograde transport or as it diffuses through the spinal fluid. We also noted that the AAV9 vector intrathecally administered is also able to cross the blood brain barrier and reach peripheral tissues such as liver, heart, etc. (FIG. 6) and is able to express the hFXN mRNA from the injected vector (FIG. 7).

The levels of FXN protein expression from the recombinant vector developed was also analyzed. Although the antibody used shows a higher affinity for the human FXN protein as seen by the protein pattern obtained after 1 hour versus overnight incubation of the blot with the primary anti-FXN antibody, FIG. 8 shows that the levels of the FXN protein expressed from the rAAV9-PGK1-FXN vector appear similar to those of the mouse FXN levels in the WT mice (FIG. 8A, lanes 3 vs. 4 and FIG. 8B second panel, lanes 3 vs. 4 and 5 vs. 6 and 7). Remarkably, we were able to detect the recombinant FXN protein in the motor cortex region (C1) of the mouse brain (FIG. 8B, lane 7). This indicates that the delivery of our vector by intrathecal injection into the lumbar region of the spinal cord results in the distribution of the vector throughout motor related regions of the CNS. In addition, the recombinant protein appears to be processed in a similar pattern as the wild-type FXN protein with the intermediate and mature form being the most prominent processed form.

We further analysed the phenotype of the YG8R hemizygous mice (Tg/−) treated with the rAAV9-PGK1-FXN compared to the rAAV9-null vector for the clasping neurological reflex and the electrophysiological properties of the caudal nerve. The clasping reflex has been shown to be involved in several neurodegenerative disorders. This reflex appears to involve sensory and also spinal motor pathways regulating the fore and hindlimb movements. In particular, the cerebello-cortico-reticular pathways have been shown to be involved. Therefore, to determine the effect of the treatment of the rAAV9-hPGK1-FXN vector on these pathways in the YG8R mice we quantified the clasping reflex at different times following the intrathecal injection of the vector (see methods). FIG. 9 shows that the YG8R mice treated with either the AAV9-null and AAV9-FXN vectors exhibit clasping defects as early as four-months of age (1.5 months after intrathecal injection). However, overtime the clasping reflex is normalized in the AAV-FXN treated mice to more closely resemble those of the WT mice even more so at 10-months of age (6.5 months after injection). This suggests that there are early anomalies in the sensory and cerebello-cortico-reticular system in the FRDA mouse model that are significantly ameliorated or reversed by the treatment with the AAV-FXN vector.

Figure 10:
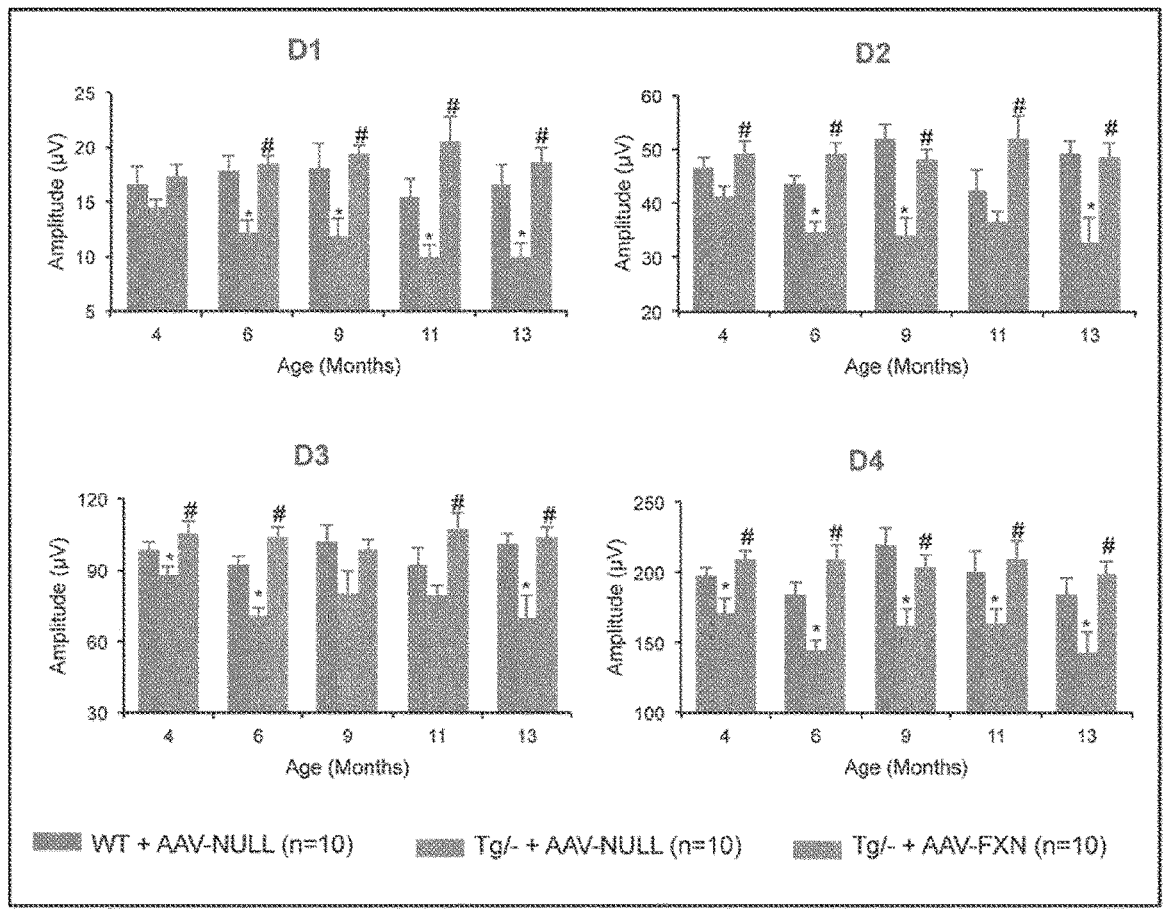

To more specifically determine the effects of the treatment on the sensory neurons we determined the electrophysiological properties (amplitude and velocity) of the caudal nerve of the YG8R mice treated with the AAV-FXN vector compared with those treated with a AAV9-null control vector. FIG. 10 shows that at all distances from the tail tip (1-4 cm) no significant differences were noted between the null vector treated WT or the null and AAV-FXN treated YG8R hemizygous mice at four months of age (1.5 months following treatment). However, from 6 months of age on, while the AAV9-null treated YG8R (Tg/−) mice showed significant decline in amplitude, the AAV9-FXN treated mice were more closely resembling the WT mice even as late as 13 months of age (9.5 months after treatment). No changes in velocity were noted (data not shown). These data indicate that the treatment with the AAV-hPGK1-FXN vector was able to preserve the function of the caudal nerve in the YG8R mice possibly by preventing loss of the axons from the affected neurons.

The invention claimed is:

1. An adeno-associated virus (AAV) vector comprising a nucleic acid, wherein the nucleic acid comprises:
   (i) a nucleic acid sequence encoding frataxin;
   (ii) a phospho-glycerate-kinase (PGK) promoter; and
   (iii) a woodchuck hepatitis virus posttranscriptional regulatory element (WPRE);
   wherein (ii) and (iii) are operably linked to and regulate the expression of (i); and
   wherein the sequence of the nucleic acid which comprises (i), (ii) and (iii) is SEQ ID NO: 4 or a sequence which is at least 95% identical to SEQ ID NO: 4.

2. The vector according to claim 1, wherein the PGK promoter comprises SEQ ID NO: 1 or a sequence which is at least 95% identical to SEQ ID NO: 1.

3. The vector according to claim 1, wherein the WPRE comprises SEQ ID NO: 2 or a sequence which is at least 95% identical to SEQ ID NO: 2.

4. The vector according to claim 1, wherein the nucleic acid sequence encoding frataxin comprises SEQ ID NO: 3, or a sequence which is at least 95% identical to SEQ ID NO: 3 and is a functional variant of frataxin.

5. The vector according to claim 1, wherein the AAV vector is an AAV serotype 9 vector.

6. The vector according to claim 1, wherein the sequence of the nucleic acid which comprises (i), (ii) and (iii) is SEQ ID NO: 4 and,
   wherein the AAV vector is an AAV serotype 9 vector.

7. A nucleic acid comprising:
   (i) a nucleic acid sequence encoding frataxin;
   (ii) a PGK promoter; and
   (iii) a WPRE;
   wherein (ii) and (iii) are operably linked to and regulate the expression of (i), and
   wherein the sequence of the nucleic acid which comprises (i), (ii) and (iii) is SEQ ID NO: 4 or a sequence which is at least 95% identical to SEQ ID NO: 4.

8. The nucleic acid according to claim 7, wherein the PGK promoter comprises SEQ ID NO: 1 or a sequence which is at least 95% identical to SEQ ID NO: 1.

9. The nucleic acid according to claim 7, wherein the WPRE comprises SEQ ID NO: 2 or a sequence which is at least 95% identical to SEQ ID NO: 2.

10. The nucleic acid according to claim 7, wherein frataxin comprises SEQ ID NO: 3, or a sequence which is at least 95% identical to SEQ ID NO: 3 and is a functional variant of frataxin.

11. A cloning vector which comprises the nucleic acid according to claim 7 and additional nucleic acid elements for promoting replication of the cloning vector in a bacterial cell.

12. A transfer vector which comprises the nucleic acid according to claim 7 and additional nucleic acid elements for promoting integration or transposition of the transfer vector into an AAV vector.

13. A pharmaceutical composition comprising the AAV vector according to claim 1 and a pharmaceutically acceptable carrier or diluent.

14. A pharmaceutical composition comprising the nucleic acid according to claim 7 and a pharmaceutically acceptable carrier or diluent.

15. A method of treatment of Friedreich's ataxia, comprising administering to a subject in need thereof an effective amount of a AAV vector according to claim 1.

16. A method of treatment of Friedreich's ataxia, comprising administering to a subject in need thereof an effective amount of the nucleic acid according to claim 7.

17. The transfer vector of claim 12, wherein the AAV vector is an AAV-9 serotype vector.

* * * * *